US006930092B1

(12) United States Patent
Barber et al.

(10) Patent No.: US 6,930,092 B1
(45) Date of Patent: Aug. 16, 2005

(54) ANTIBIOTIC AGENTS

(75) Inventors: Jill Barber, Didsbury (GB); Mohammed N. Mordi, Cheetham Hill (GB)

(73) Assignee: The Victoria University of Manchester, Manchester (GB)

( * ) Notice: Subject to any disclaimer, the term of this patent is extended or adjusted under 35 U.S.C. 154(b) by 0 days.

(21) Appl. No.: 10/018,467

(22) PCT Filed: Jun. 19, 2000

(86) PCT No.: PCT/GB00/02217

§ 371 (c)(1),
(2), (4) Date: Apr. 4, 2002

(87) PCT Pub. No.: WO00/78772

PCT Pub. Date: Dec. 28, 2000

(30) Foreign Application Priority Data

Jun. 19, 1999 (GB) .................................... 9914346

(51) Int. Cl.[7] .................... A61K 31/70; C07H 17/08

(52) U.S. Cl. ...................................... 514/29; 536/7.2

(58) Field of Search ........................ 536/7.2; 514/29

(56) References Cited

U.S. PATENT DOCUMENTS 2,862,921 A * 12/1958 Booth ..................... 536/7.2
3,878,192 A *  4/1975 Blasina et al. ........... 536/7.2

FOREIGN PATENT DOCUMENTS

| EP | 0 553 353  | 8/1993 |
| WO | WO 98/33482 | 8/1998 |

OTHER PUBLICATIONS

Martin et al, "Chemical modification of erythromycin antibiotics, 4. Structure-activity relations of erythromycin esters", J. Med. Chem. 15(6):635-638 (1972).

Omura et al, "Research and development of clarithromycin", Yakugaku Zasshi 112(9):593-614 (1992).
Jones et al, Chemical modifications of erythromycin antibiotics. 3. Synthesis of 4" and 11 esters of erythromycin A and B, J. Med. Chem. 15(6):631-634 (1972).
Ono et al, "Drug resistance in *Staphylococcus aureus*. Induction of macrolide resistance by erythromycin, oleandomycin and their derivatives", Jpn. J. Microbiol. 19(5):343-347 (1975).
Bojarska-Dahlig et al, "Quantitative structure-activity relationships in erythromycin group with MTD technique", Pol. J. Pharmacol. Pharm. 33(3):359-363 (1981).
Kibwage et al, "Antibacterial Activities of Erythromycins A B C and D and Some of Their Derivatives", Antimicrobial Agents and Chemotherapy 28(5):630-633 (1985).
Cane et al, "Macrolide biosynthesis, 3. Stereochemistry of the chain-elongation steps of erythromycin biosynthesis", J. Am. Chem. Soc. 108(16):4957-4964 (1986.
Mordi et al, "Acid-Catalyzed Degradation of Clarithromycin and Erythromycin B: A Comparative Study Using NMR Spectroscopy", J. Med. Chem. 43(3):467-474 (2000).
Bojarska-Dahlig, "Correlation of physiochemical parameters and antibacterial activity of macrocyclic antibiotics", Abh. Akad. Wiss. DDR, Abt. Math. Naturwiss., Tech. (2N, Quant. Struct.-Act. Anal.), pp. 343-349 (1978).
Natl Coord Group Invest Short-Course Chemother: "Short Course Chemo Therapy in Pulmonary Tuberculosis", Chin. J. Tuberc. Respir. Dis. 5(2):78-81 (1982).

* cited by examiner

*Primary Examiner*—Elli Peselev
(74) *Attorney, Agent, or Firm*—Nixon & Vanderhye P.C.

(57) ABSTRACT

Methods of treating a microbial infection comprising administering to a patient in need of such treatment are disclosed. In one aspect the method comprises administering to a patient in need of such treatment a therapeutically effective amount of Erythromycin B (or a pharmaceutically acceptable derivative thereof). In another aspect the method comprises a pharmaceutical composition comprising at least 50% by weight of Erythromycin B (or a pharmaceutically acceptable derivative thereof) of the total weight of antibiotic present in the composition. Also disclosed are 2'-esters of Erythromycin B and Erythromycin B enol ether.

20 Claims, 24 Drawing Sheets

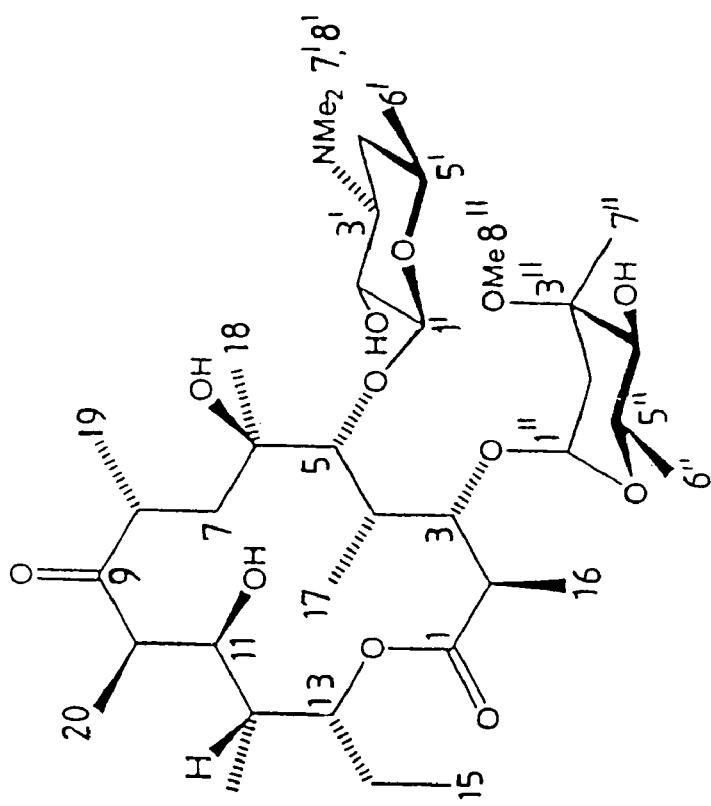
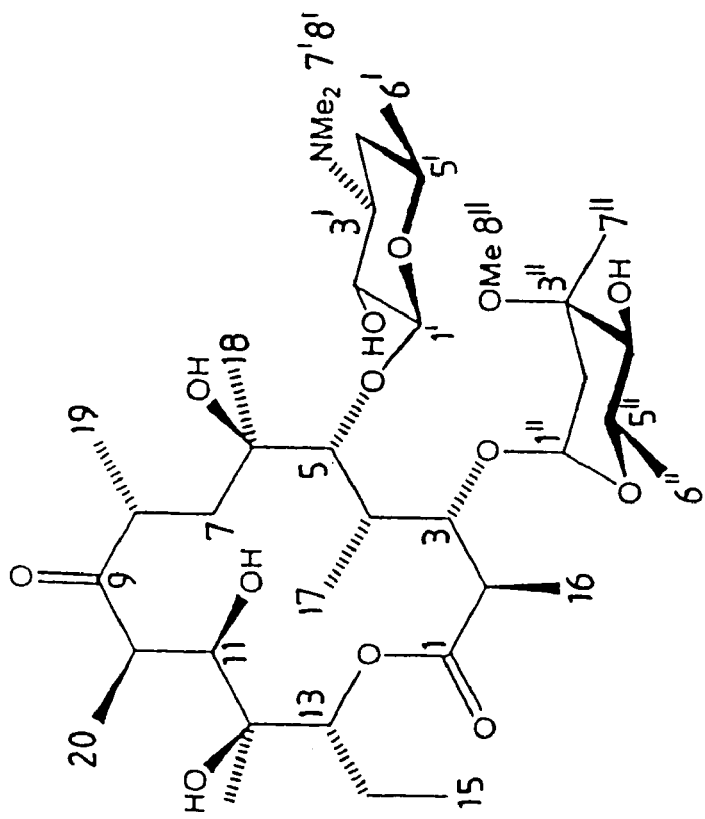
FIG. 1
1 - Erythromycin A
4 - Erythromycin B

3 - Azithromycin

2 - Clarithromycin

5 — Erythromycin A ethyl succinate

Decomposition pathway for erythromycin A in aqueous acidic medium

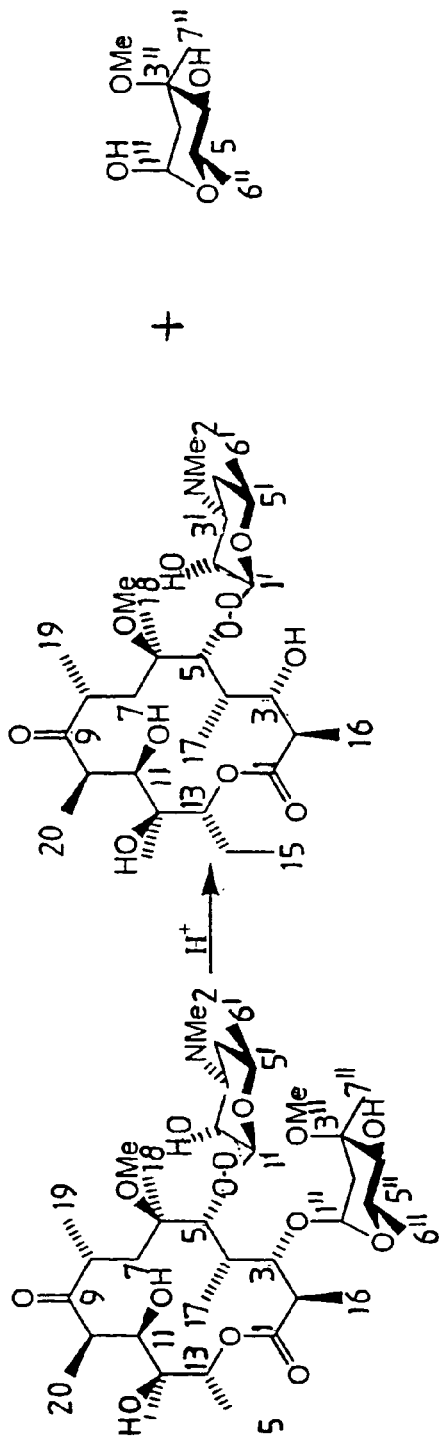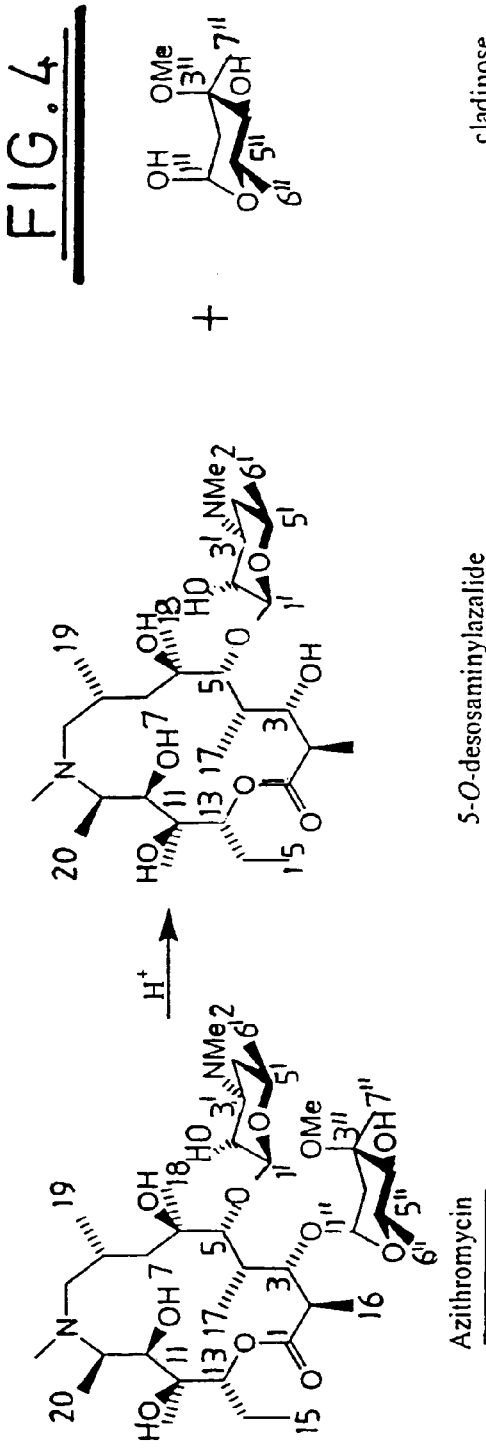
FIG. 4
Decomposition pathway for Clarithromycin and the azalide, Azithromycin, in acidic aqueous medium FIG. 7 A stack of 1D 1H NMR spectra of erythromycin B, degrading to its decomposition product, 5-deB at pH 2.5, 55°C Plot of percentage remained/accumulated in the degradation solution for erythromycin B (eB), 5-deB and the total amount of both erythromycin B and 5-deB (5-deB + eB) in Britton-Robinson buffer, pH 2.5, 59°C Plot of percentage remained/accumulated in the degradation solution for erythromycin B (eB), 5-deB and the total amount of both erythromycin B and 5-deB (5-deB + eB) in Britton-Robinson buffer, pH 2.5, and 35°C (A) and 45°C (B)

FIG. 11 ESI-MS spectrum of erythromycin B following degradation in aqueous acidic condition at 37 °C showing signal of its degradation product; 5-O-desosaminyl-erythronolide B (MH+, m/z 561).

ROESY spectrum at 30°C from degradation mixtures of erythromycin B, containing 5-deB and cladinose Electrospray-Mass spectrum (in positive mode) of erythromycin B (MW 717), 5-deB (MW 559) and cladinose (MW 157) in protiated buffer, pH 2.5. Please note that the actual mass of every compounds should be less 1 mass unit from the values shown in the spectrum.

FIG. 17 A stack of 1D 1H NMR spectra of 5-deB, pH 2.5, incubated at 55°C

A stack of 1D1H NMR spectra (the downfield 0.8-1.35ppm) of 5-deB, pH2.5, incubated at 55°C, showing a doublet signal at δ1.15 was transformed to a singlet signal at δ1.14

FIG. 20 1D1H NMR spectrum of erythromycin B enol ether in aqueous buffer, pH 2, degraded at 37°C for 10min 1D 1H NMR spectrum of erythromycin B enol ether in aqueous buffer, pH 7, degraded at 37°C for 80min

ANTIBIOTIC AGENTS

This application is the US national phase of international application PCT/GB00/02217, filed 19 Jun. 2000, which designated the U.S. and claims priority to GB Application No. 9914346.3, filed 19 Jun. 1999. The entire contents of these applications are incorporated herein by reference.

The present invention relates to antibiotic agents and more particularly such agents which overcome disadvantages associated with erythromycin A.

This specification comprises FIGS. 1 to 23 of drawings. Of these, FIGS. 1 and 2 comprise Formulae Sheets incorporating the formulae to which reference is made below.

The actinomycete *Saccarropolyspora erythra* produces erythromycin A (1) and several of its biosynthetic precursors (erythromycins B–F). Erythromycin A is one of the most widely used and important antibacterial agents in current clinical use. The other erythromycins, most notably erythromycin B, are also antibacterial agents of varying potency, but are not used in clinical practice.

Erythromycin A, despite its clinical utility, has several undesirable properties. It has a vile taste, causing a degree of poor compliance in children. No amount of work on paediatric formulations has yet successfully masked the taste. It and its degradation products cause severe gastric disturbance in sensitised adults, leading again to poor compliance. The drug and its degradation products are processed by cytochrome P450 enzymes in the liver, which are also responsible for processing other drugs including common hay fever remedies. Erythromycin A and its by-products are able to saturate these enzymes, so that the blood levels of the other drugs rise, leading to overdose.

All of these problems arise in large part because erythromycin A is extremely acid sensitive. It has a half-life of about an hour at pH 4.6 and 60° C.[2]. Thus large doses (up to 2 g per day) are required for efficacy, because a high proportion of the administered drug is degraded in the acid conditions of the stomach. One of the products of erythromycin A degradation is the spiroketal as shown in the decomposition pathway illustrated in FIG. 3[3,4] of the accompanying drawings. The degradation products do not have antibacterial activity, but they do cause gastric disturbance and are metabolised in the liver.

In the last few years, two derivatives of erythromycin A have appeared in the clinic. They are clarithromycin (2) and azithromycin (3). Both of these compounds are made from erythromycin A but have the disadvantages of requiring several synthetic steps for their production. Clarithromycin is unable to cyclise in the 6,9 direction because the 6-hydroxy group is methylated. Azithromycin is unable to cyclise at all because C9 has been modified. Both are acid-sensitive, but much less so than erythromycin A. Typical recommended dose rates are 500 mg per day (divided into two doses) for 5 days (clarithromycin) and 500 mg per day (in one or two doses) for 3–5 days (azithromycin), rather than typically 1 g to 2 g per day administered in 4 doses for 7–12 days as with erythromycin A. It is reasonable to regard both of these compounds as "acid-stable erythromycin A". The degradation pathway for these compounds has been explored and involves expulsion of the cladinose sugar in both cases (FIG. 4).[5,6]

The present invention seeks to obviate or mitigate the above-mentioned disadvantages by providing alternative antibacterial agents to Erythromycin A, clarithromycin and azithromycin.

According to one aspect of the present invention there is provided Erythromycin B (or a pharmaceutically acceptable derivative thereof) for use in therapeutic administration for the treatment of microbial (e.g. bacterial) infection.

We have found that Erythromycin B (4), a biosynthetic precursor of erythromycin A, has advantages over erythromycin A, clarithromycin and azithromycin. In vitro it has similar antibacterial activity to erythromycin A.[1] It lacks the 12-hydroxy function and therefore cannot cyclise in a 12,9 direction; (12-9 cyclisation is the first step of acid-catalysed degradation) It is not overly simplistic to regard erythromycin B as a mirror image of clarithromycin. We have carried out degradation studies under acid conditions on erythromycin B and shown that (i) the mechanism of degradation involves loss of the cladinose sugar in the same way as clarithromycin and azithromycin and (ii) that the drug is much more stable than erythromycin A. Its stability is comparable with that of clarithromycin and azithromycin.

Erythromycin B (or derivative) has the further advantage as an acid-stable antibiotic in that it is a fermentation product and therefore avoids the synthetic steps employed in the manufacture of clarithromycin and azithromycin. Furthermore, the vile taste common to the macrolide antibiotics can be readily masked in the case of Erythromycin B and its derivatives using existing inexpensive technology.

Erythromycin B is currently not used in clinical practice but our stability studies indicate that it would be a very suitable replacement for Erythromycin A, clarithromycin and azithromycin in many circumstances. Thus, Erythromycin B (or derivative) may be used for treating a microbial (e.g. bacterial) infection by administering to a patient in need of such treatment a therapeutically effective amount of Erythromycin B (or derivative). In view of its enhanced stability compared to Erythromycin A, Erythromycin B (or derivative) may be used in lower dosage rates. Erythromycin B (or derivative) may be used in an amount up to 500 mg (e.g. 250 to 500 mg) per day as compared to 2 g per day as generally employed for Erythromycin A.

According to another aspect of the present invention, there is provided an antibiotic composition comprising at least 50% by weight of Erythromycin B (or a pharmaceutically acceptable derivative thereof) based on the total weight of antibiotic present in the composition.

Preferably the antibiotic composition comprises at least 75% by weight of Erythromycin B (or derivative), most preferably at least 90%, on the same basis as defined in the previous paragraph.

Suitably the composition will contain only Erythromycin B (or derivative) as antibiotic.

The composition of the invention may contain between 50 mg and 1 g, preferably 100 mg to 500 mg Erythromycin B (or derivative).

The composition will incorporate a pharmaceutically acceptable vehicle and may be in any suitable form known in the art, suitably tablet, capsule, suspension, elixir, syrup or as an injectable. A tablet containing 250 mg or 500 mg of Erythromycin B (or derivative thereof) is most preferred.

In the manufacture of paediatric formulations, erythromycin A and its derivatives are normally esterified at the 2' position to give compounds such as erythromycin A ethyl succinate (5). Similar derivatives of clarithromycin have not yet appeared.

In accordance with a further aspect of the present invention there are provided 2'-ester derivatives of Erythromycin B or of Erythromycin B enol ether. The invention also provides an antibiotic formulation comprising a therapeutically effective amount of such an ester, preferably in conjunction with a pharmaceutically acceptable vehicle.

The esters may be derived, for example, from any mono- or dicarboxylic acid. A preferred example of a mono- or dicarboxylic acid is succinic acid, which leads to the formation of a succinate mono- or di-ester. The ester may be used for the treatment of microbial (e.g. bacterial) infections by administering a therapeutically effective amount of the ester to a patient in need of treatment.

The administration of the 2'-ester derivatives may be as described above for administration of Erythromycin B and its derivatives. Thus, for example, the 2'-ester may be provided in a pharmaceutical composition containing at least 50% by weight of the 2'-ester based on the total weight of antibiotic in the composition.

All of the active agents disclosed herein may be used for a treatment of a wide range of microbial (e.g. bacterial) infections. Examples include TB, Syphilis, *Helicobacter pylori*, or Chlamydia. The agents may alternatively or additionally be used for the treatment of any condition for which a penicillin would normally be employed and have advantages in that they may be used for the treatment of penicillin sensitive patients.

BRIEF DESCRIPTION OF THE DRAWINGS

FIG. 4. Decomposition pathway for Clarithromycin and the azalide, Azithromycin, in acidic aqueous medium.

(FIG. 9A) and 45° C. (FIG. 9B).

Figure 1:
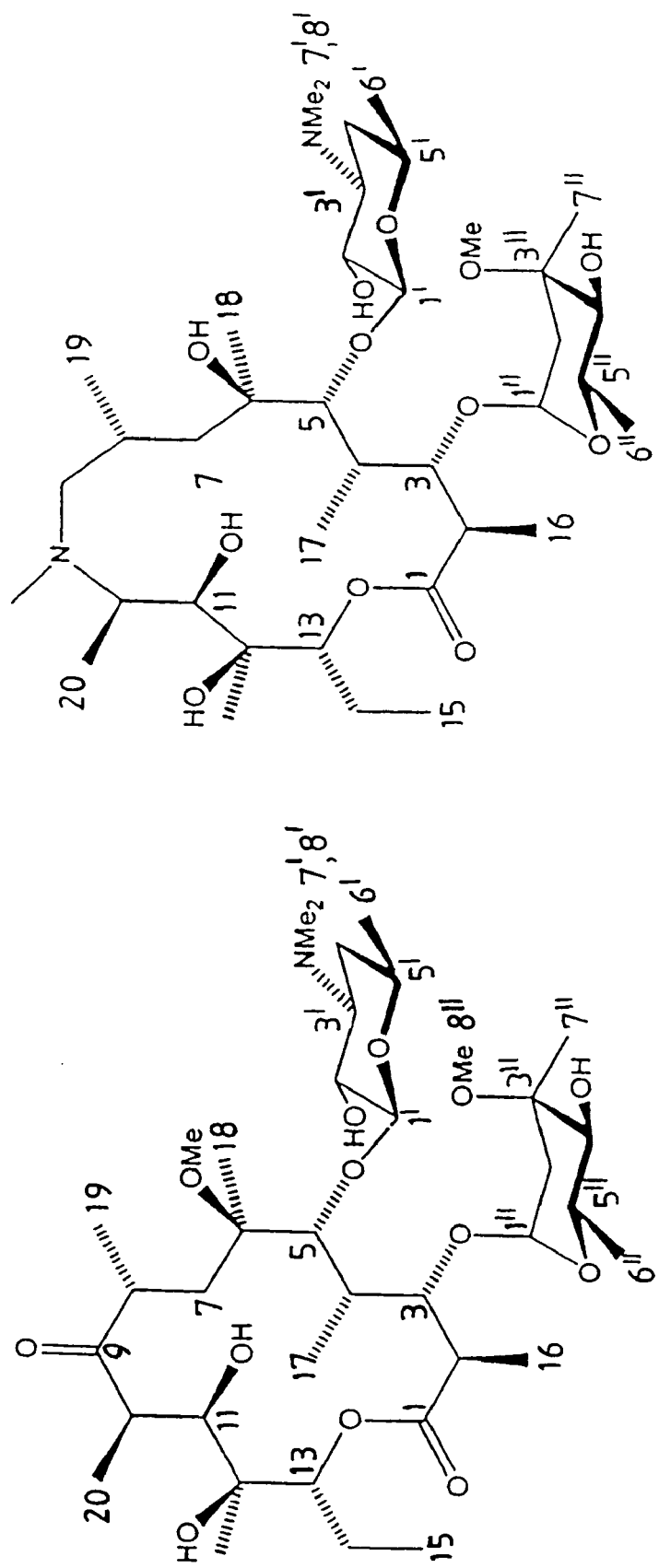
FIG. 1. Structures for 1-Erythromycin A, 4-Erythromycin B, 2-Clarithromycin and 3-Azithromycin.

The invention is illustrated by way of example only by the following Experimental Section and accompanying FIGS. 5 to 23 of the drawings.

Experimental Section (i) Background

The effective buffer range for a weak acid and base is approximately from pH=pKa+1 to pH=pKa−1 (a range of 2 pH units). The buffering ability increases (a wider pH) range when two or more buffers are present (additive effects). Furthermore, if a buffer system has several successive pKa values which differ by 2 pH units, approximately linear buffer capacity could be obtained (Perrin & Dempset, 1987). Several universal buffers have been established such as citric acid-phosphate buffer for pH2.6–8 (McIlvaine, 1921), piperazine-glycylglycine buffer for pH 4.4–10.8 (Smith & Smith, 1949) and Britton-Robinson buffer for pH2.6–12 (Britton & Robinson, 1931).

Alam (1996) has shown that phosphate and acetate buffers are not suitable for low pH studies. He used Britton-Robinson buffer pH2, as the medium for the degradation of Azithromycin. It is a universal buffer, relatively inexpensive and its deuteriated components are readily available, or can be prepared in the laboratory. It is convenient to use deuteriated buffer species in the NMR application as they are lacking in protons.

In our studies, samples of erythromycin B (4 mM) were prepared in deuteriated Britton-Robinson buffer (4 mM) at apparent pH 2.5. This initial degradation experiment has been set up to form the buffering capacities of 4 mM Britton-Robinson buffer at pH 2.5. The apparent pHs of samples were determined over time. It was found that the apparent pH of 2.5 was maintained during the course of the degradation. The results suggest that the Britton-Robinson buffer is giving adequate buffering to the system at lower pH. This finding is consistent with the fact that Britton-Robinson has been widely used as a versatile buffer, buffering a system as low as pH 0.3 and as high as pH 13 (Barroso et al., 1995).

(ii) Degradation Studies of Erythromycin B

Almost all drugs are subject to some form of degradation. In pharmaceutical applications, it is a standard procedure to study the degradation of medicinal compounds at extreme temperature and then extrapolate the information to other temperature conditions. Where NMR technique is used, degradation studies should be completed in a reasonable time period, because of the expense of instrument time. As a set of spectra is required to generate a good degradation profile of any particular compound, conditions should be established so that the degradation occurs at a reasonable rate yet not too fast, as a good noise-to-signal ratio needs a few minutes to be accomplished. In this experiment, spectra were initially measured every 5 min. Corresponding to 32 scans pulsing every 6 sec.

Several degradation studies involving erythromycin A have been carried out at different buffers, ionic strength, temperatures and pHs employing HPLC-UV technique (Cachet et al., 1989; Atkins et al., 1986) and NMR spectroscopy measurement (Alam et al., 1996). All the studies showed that the rate of decomposition was very dependent on the pH and temperature.

Erythromycin A in 50 mM formate buffer pH 4 decomposed almost completely within 4 hours at 37° C. (Atkinson et al, 1986). Another study showed that erythromycin A in 50 mM acetate buffer pH 4.6, degraded at 60° C. to completeness within 3 hours (Alam, 1996). Furthermore, by reducing the pH and temperature to 3.5 and 35° C. respectively, erythromycin A degraded substantially even before the first spectrum was recorded (Alam, 1996). Based on those observations and the fact that erythromycin B lacks the hydroxyl group at position 12 which is believed to be important for its better stability, pH 4.6 was chosen as the initial pH in the degradation of erythromycin B. It was found that, at pH 4.6, degradation occurred very slowly and it was not sensible to monitor its rate of degradation. Further studies showed that decomposition of erythromycin B at pH 2.5 was completed in reasonable time periods depending on the temperature used (6–12 hr).

A full kinetics decomposition of erythromycin B study was carried out in Britton-Robinson buffer pH 2.5 at temperatures of 35, 40, 45, 50 and 55° C. Initially, array $1D^1H$ NMR spectra were acquired either every 5 min, corresponding to 32 scans pulsing every 6 sec and dummy scans of 18 (for 45, 50 and 55° C. experiments) acquired every 10 min, corresponding to 32 scans pulsing every 10 sec with dummy scans of 28 (for 35, 40 and 45° C. experiments). Once the experiment had proceeded for an hour, NMR spectra were acquired less frequently by increasing the numbers of dummy scans used.

Figure 5:
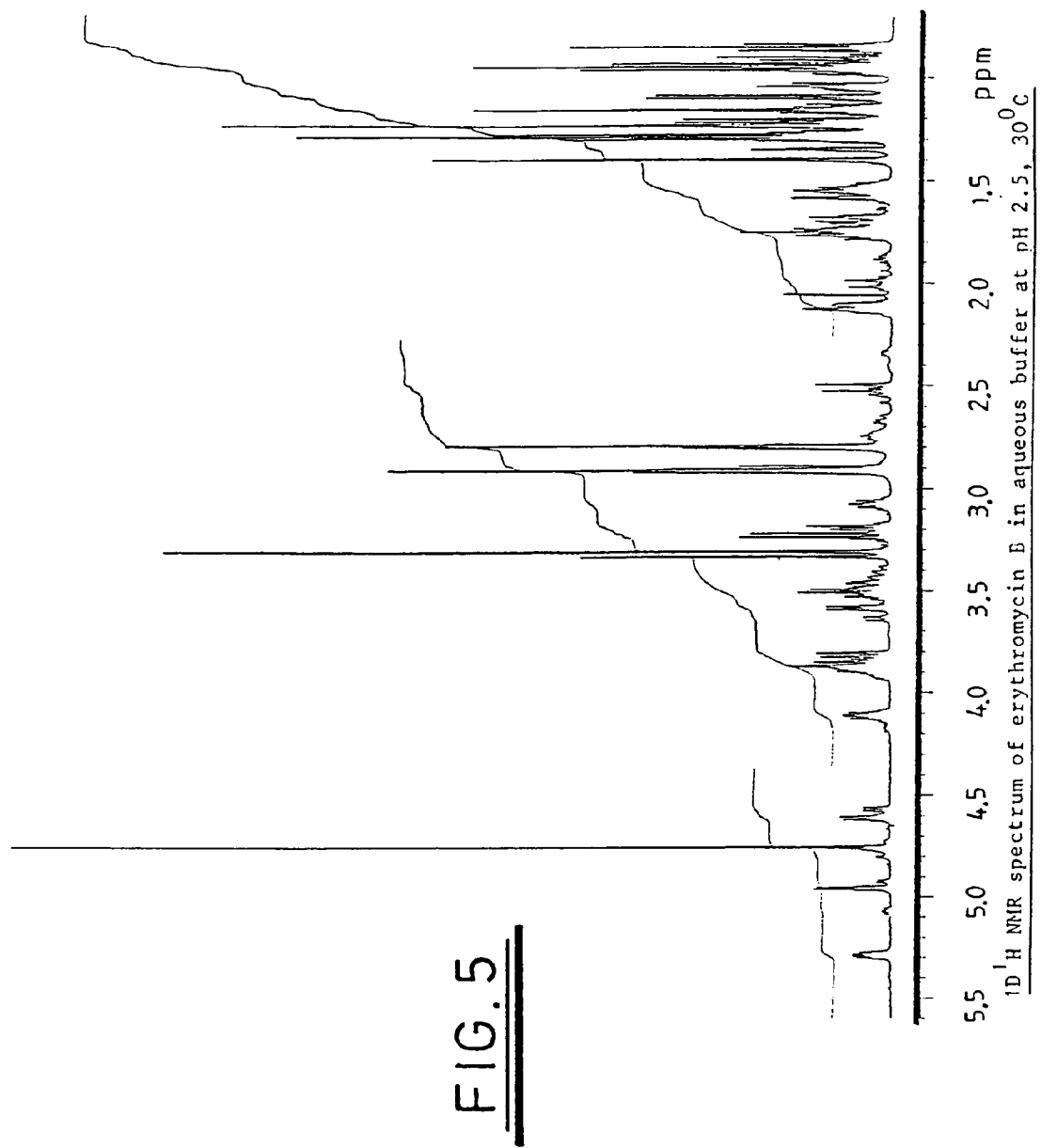
FIG. 5. $1D^1H$ NMR spectrum of Erythromycin B in aqueous buffer at pH 2.5, 30° C.
Figure 6:
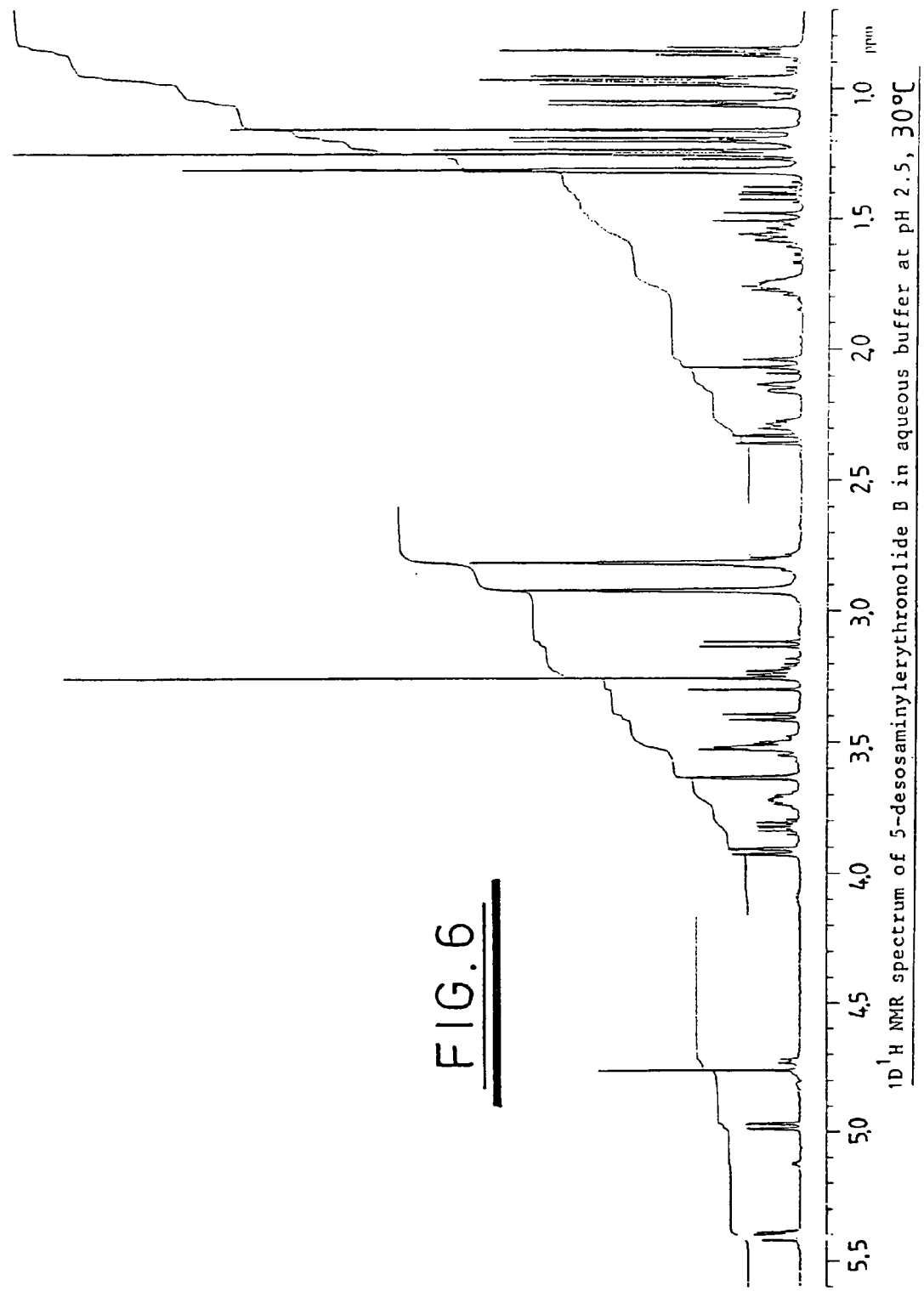
FIG. 6. $1D^1H$ NMR spectrum of 5-desosaminylerythronolide B in aqueous buffer at pH 2.5, 30° C.
Figure 7:
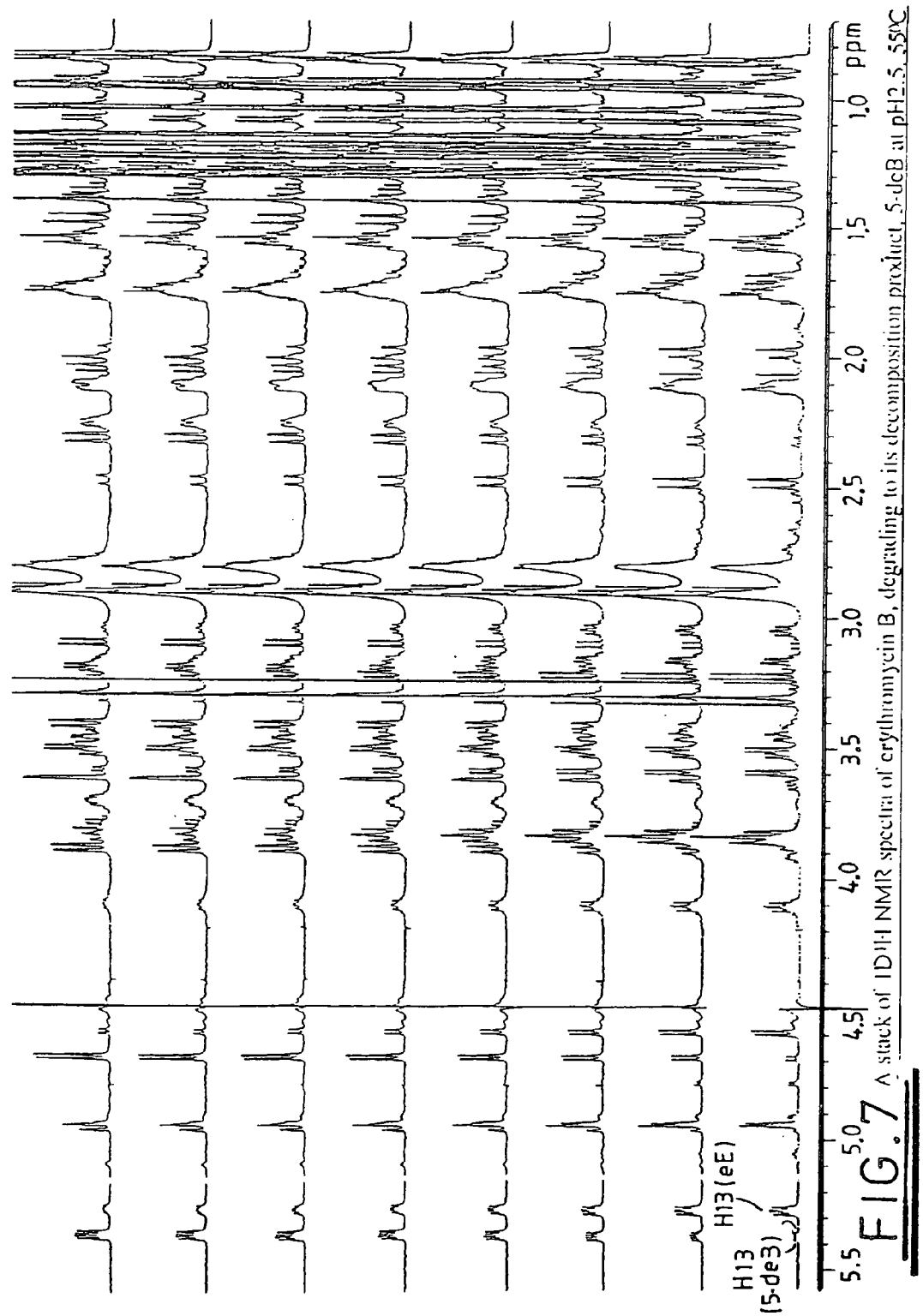
FIG. 7. A stack of $1D^1H$ NMR spectra of Erythromycin B, degrading to its decomposition product, 5-dcB at pH 2.5, 55° C.

The $1D^1H$ spectrum of erythromycin B at pH 2.5 showed distinct peaks pattern when compared to the spectrum of fully degraded samples which were later identified as 5-desosaminyl erythronolide B (5-deB). The differences in the spectra were characterised by the distinctive coupling constants and chemical shifts of signals in erythromycin B and 5-deB which could be used to monitor the degradation of erythromycin B. The distinct peaks whose disappearance in erythromycin B and the appearance in 5-deB could be monitored comfortably were signals of H13, H1' and H5"; the chemical shifts changed from δ5.29 to δ5.40, δ4.60 to δ4.97 and δ4.44 to δ4.73, respectively. The typical $1D^1H$ NMR spectra of erythromycin B and 5-deB in Britton-Robinson buffer, apparent pH 2.5, are depicted in FIGS. 5 and 6 respectively.

Figure 8:
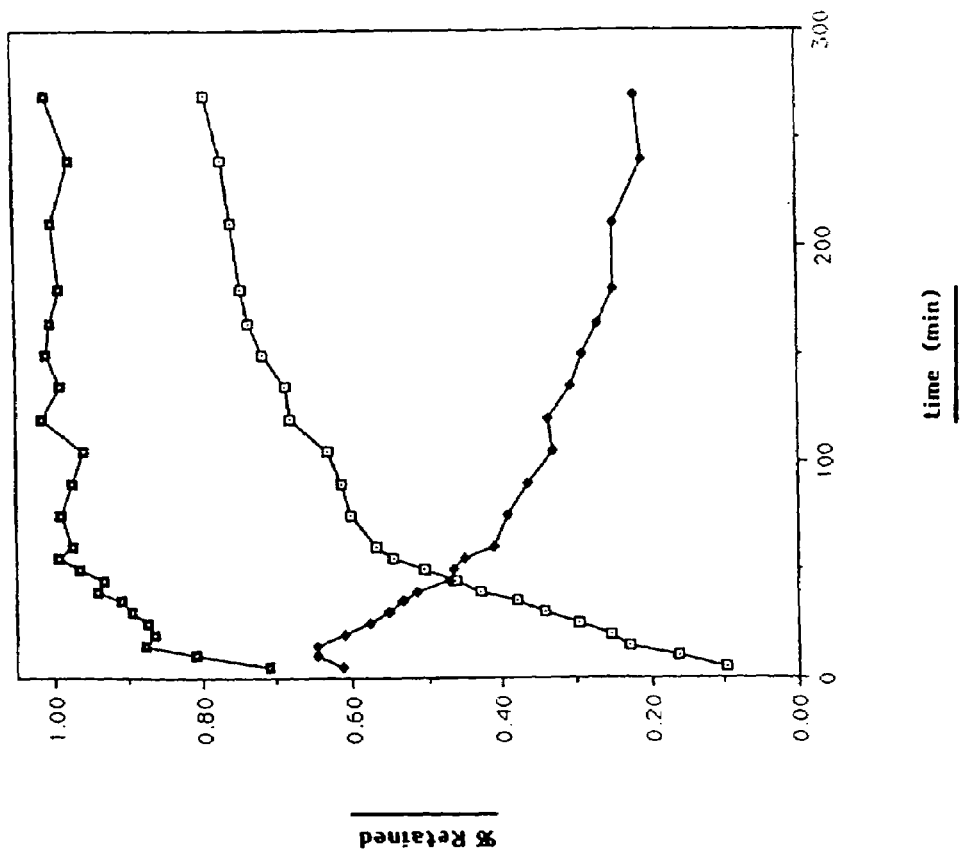
FIG. 8. Plot of percentage remained/accumulated in the degradation solution for Erythromycin B (eB), 5-deB and the total amount of both Erythromycin B and 5-deB (5-deb+eB) in Britton-Robinson buffer, pH 2.5, 55° C.

A degradation profile of erythromycin B was constructed by observing the disappearance of signal H13 at δ5.29, whilst for the product (5-deB) accumulation, H13 signal at δ5.40 was chosen. A set of degradation spectra at 55° C. is presented in FIG. 7. From the spectra, it is clearly observed that H13 of erythromycin B decreased over the time, while at the same time the H13 of 5-deB increased. The degradation profile was then plotted by using the integral values of erythromycin B and 5-deB, and this profile is depicted in FIG. 8. TSP was used as the marker for consistency of the degradation experiment as its integral value did not change during the degradation course and its peak also did not interfere with the signals of the compounds.

Figure 9:
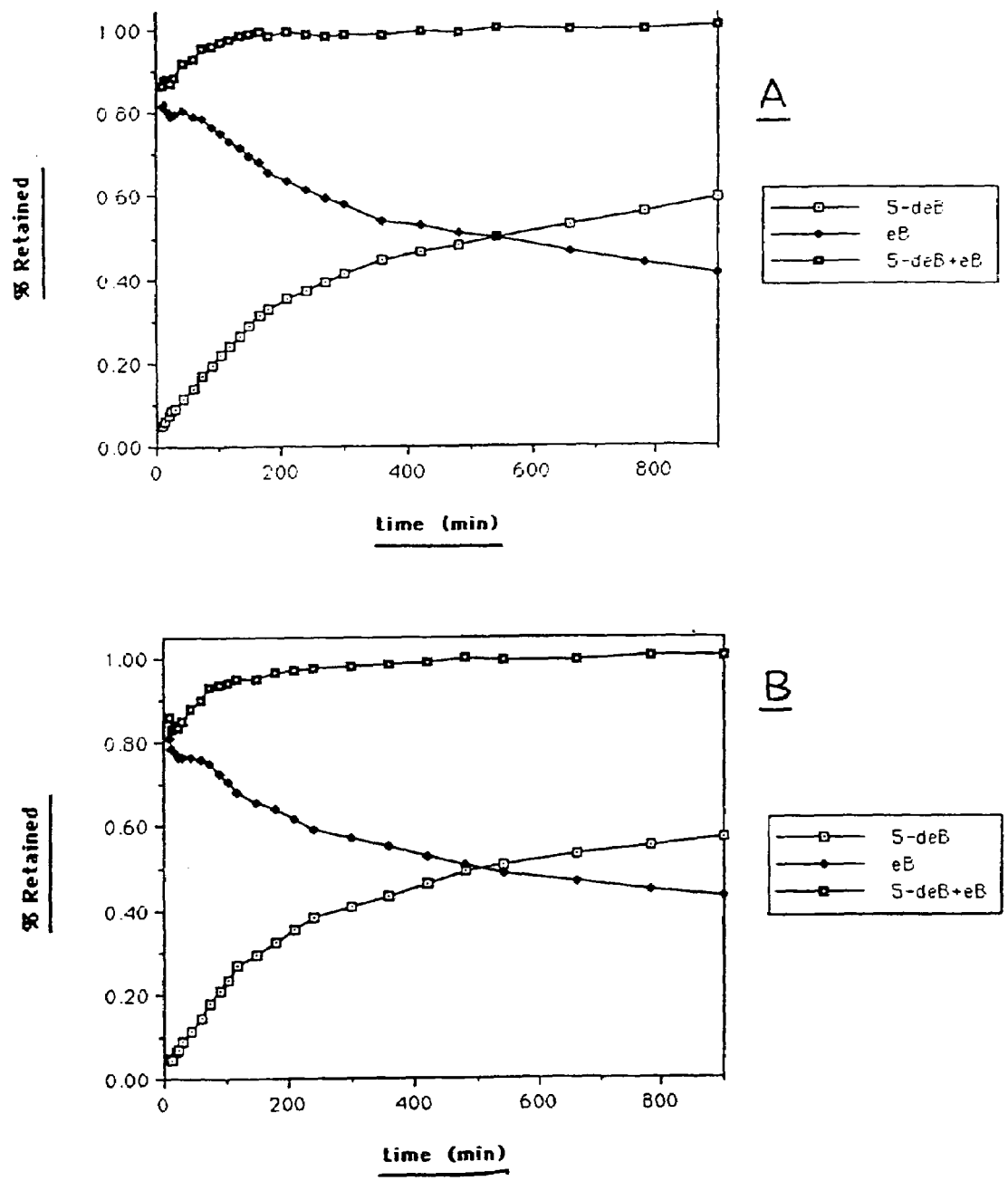
FIGS. 9A and 9B. Plot of percentage remained/accumulated in the degradation solution for Erythromycin B (eB), 5-deB and the total amount of both Erythromycin B and 5-deB (5-deB+eB) in Britton-Robinson buffer, pH 2.5, and 35° C.

As shown in FIG. 8, the concentration of erythromycin B decreased exponentially whilst the concentration of 5-deB shows fairly similar increase in the magnitude. However, when the mass of both compounds was added together, the total mass was not maintained all the time. In the first portion of the degradation course, the total mass of erythromycin B and 5-deB increased over time and was followed by a plateau. The same pattern of degradation was also demonstrated at 35 and 45° C. and the profile is depicted in FIG. 9. These results suggest, at the beginning of degradation reaction, a mass balance was not conserved due to the existence of the third compound which participates in the reaction. This intermediate compound was later identified as erythromycin B enol ether (eBee).

(iii) Deuteriation Effect at C8

Figure 10:
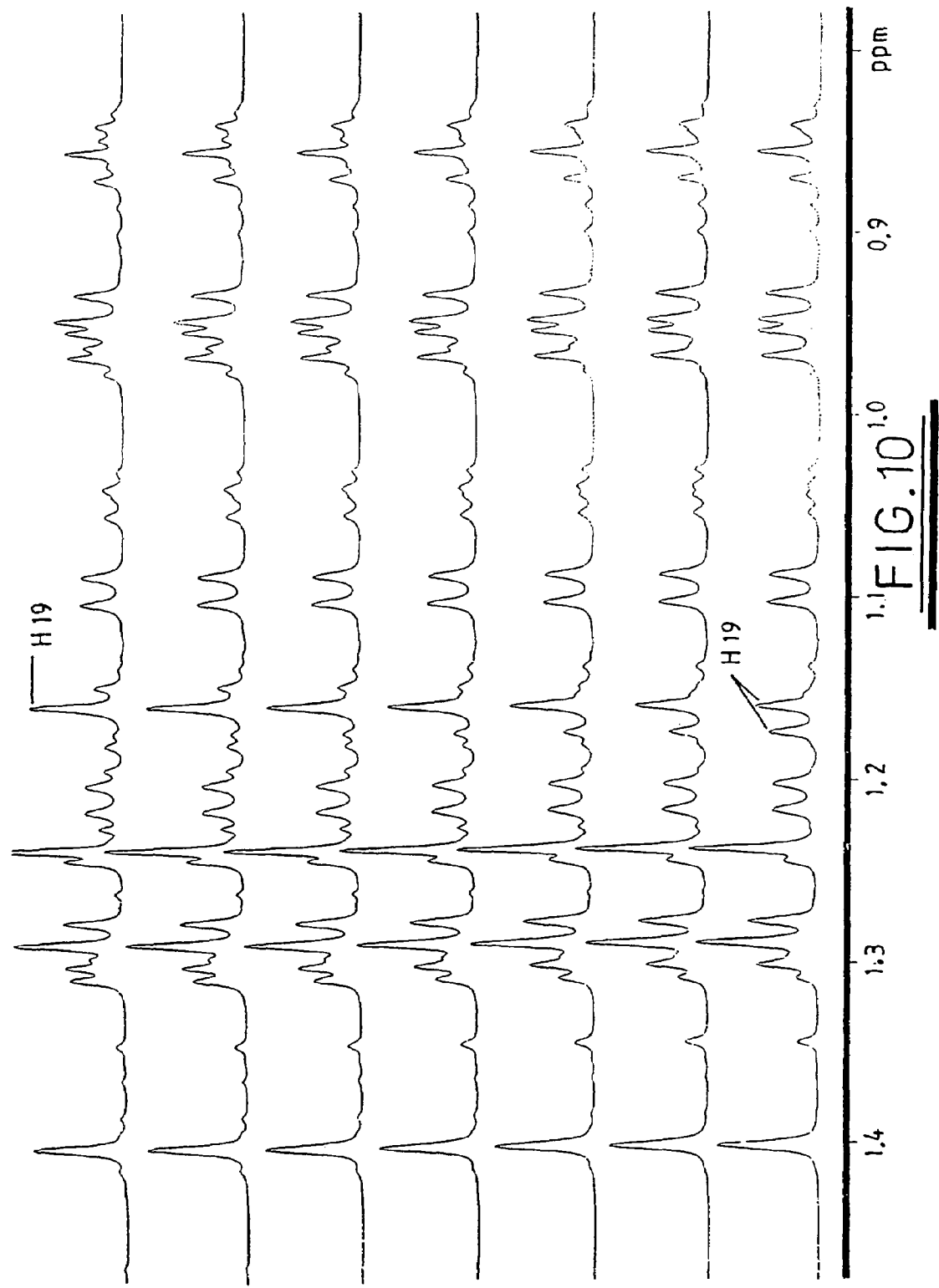
FIG. 10. A set of spectra demonstrating the deuteriation of Erythromycin B at 40° C.
Figure 11:
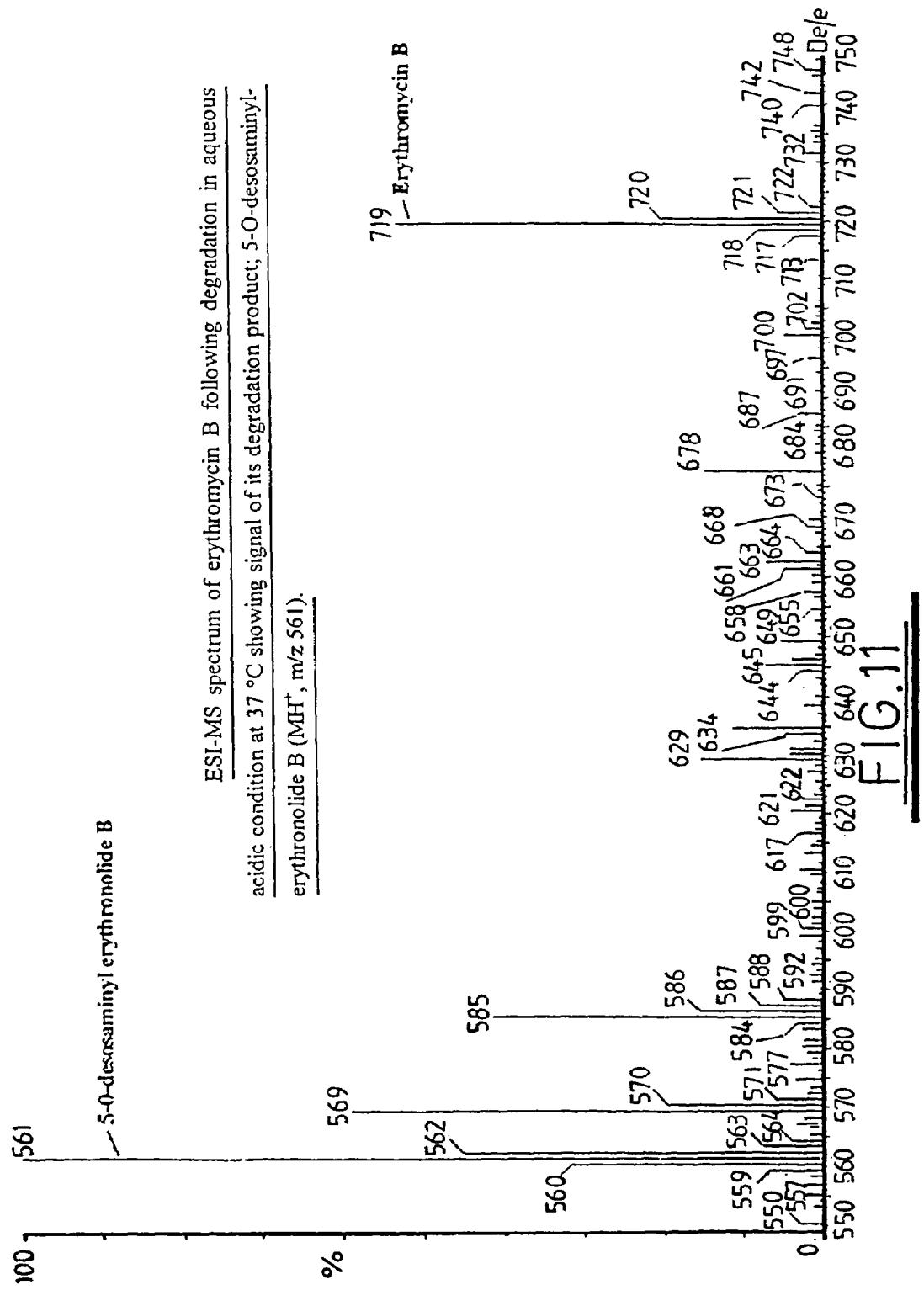
FIG. 11. ESI-MS spectrum of Erythromycin B following degradation in aqueous acidic condition at 37° C. showing signal of its degradation product; 5-O-desosaminylerythronolide B ($MH^+$, m/z 561).
Figure 12:
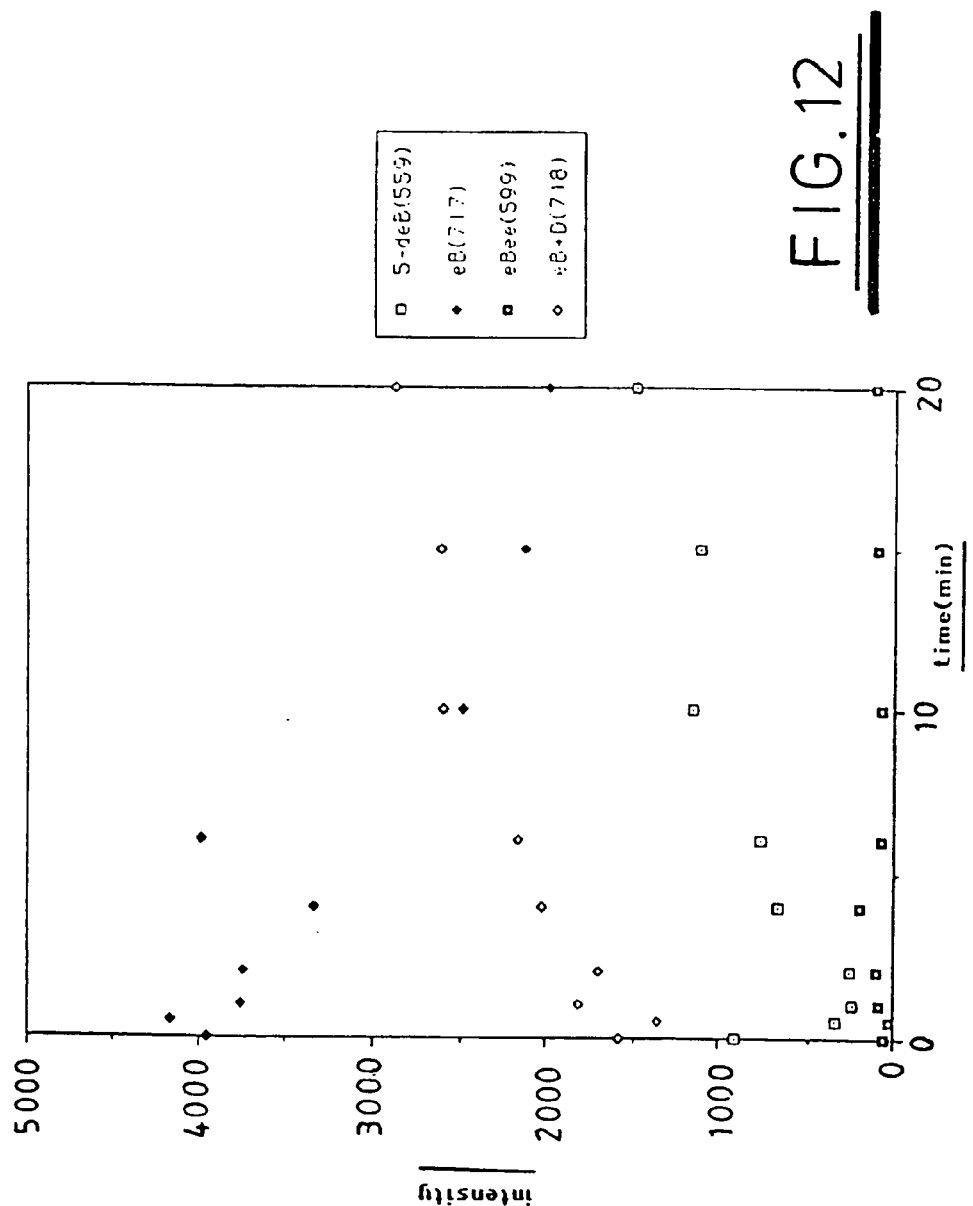
FIG. 12. Plot of intensity of Erythromycin B (eB, MW 717), Erythromycin B-Deutron (eB+D), MW 718), eBec (MW 599) and 5-deB (MW 559) during the degradation of Erythromycin B to 5-deb at ph 2.5, 55° C.
Figure 13:
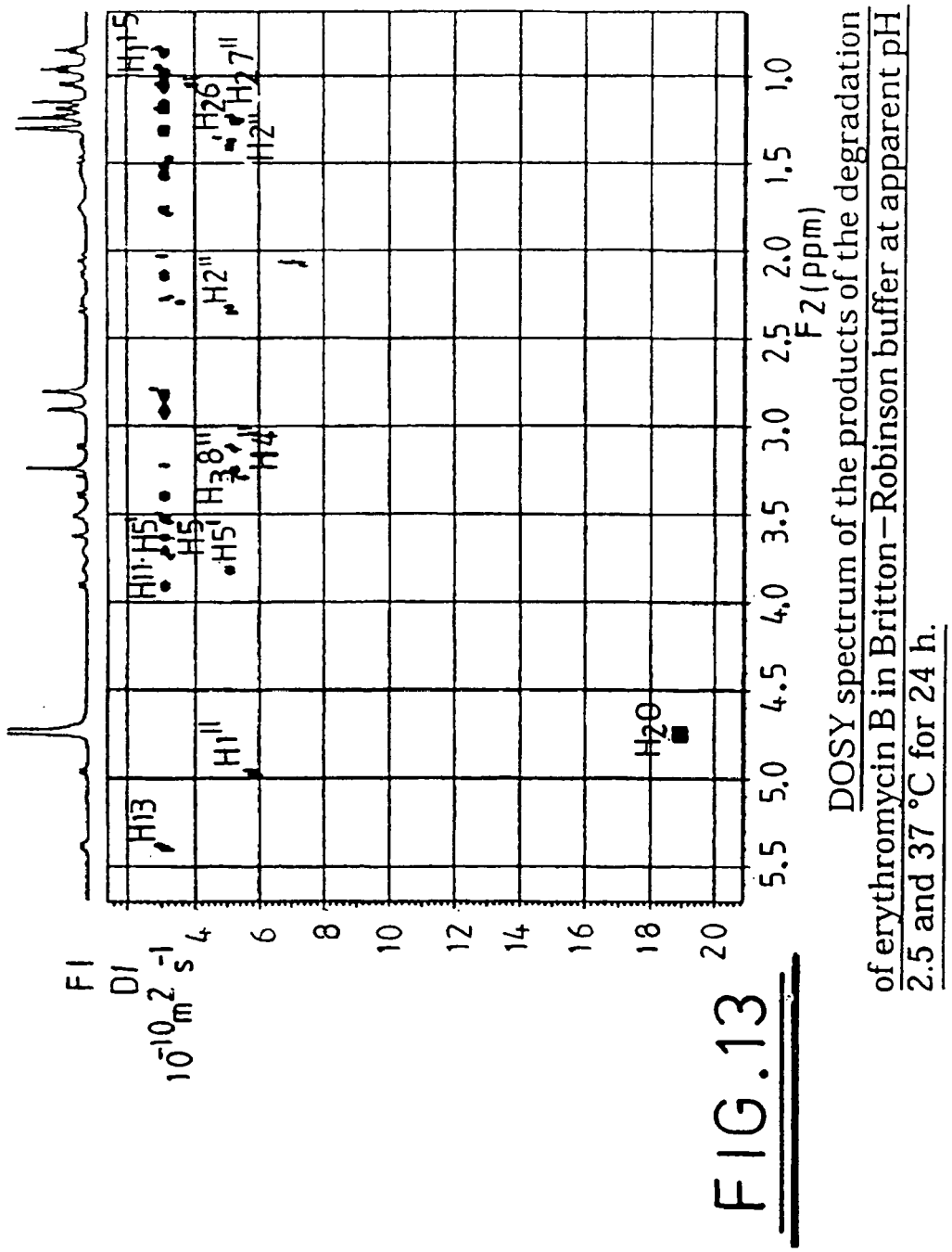
FIG. 13. DOSY spectrum of the products of the degradation of Erythromycin B in Britton-Robinson buffer at apparent pH 2.5 and 37° C. for 24 h.

During the degradation course of erythromycin B, deuteriation at C8 (H8 has been replaced with deuterium atom, D8) has been observed in the $1D^1H$ spectra. Thus, the $H_319$ which appeared initially as a doublet at δ1.17 has been transformed to a singlet at δ1.16. A set of spectra demonstrating the deuteriation of erythromycin B at 40° C. is shown in FIG. 10. By using an electrospray-mass spectrometry (EM-MS) technique, this effect was clearly observed and a typical MS chromatogram showing the peaks of erythromycin B (MW 717), erythromycin B–D (MW 718) and the degradation product, 5-deB (MW 559) is presented in FIG. 11. (Note that the actual mass of every compound should be less 1 mass unit from the values shown in the spectrum). Therefore, a deuteriation and/or degradation profile of erythromycin B at 55° C. based on ES-MS study was plotted and is shown in FIG. 12. This plot suggests that at time zero (apparent degradation should not occur), some erythromycin has already been deuteriated and its amount was increased over time and the appearance rate of both erythromycin B–D and 5-deB were quite similar.

At this point, it is difficult to postulate whether the deuteriation involves the degradation of erythromycin B to 5-deB, or if it is just an instantaneous reaction between erythromycin B and its deuteriated buffer.

(iv) Identification of Degradation Product

In this study we employed an NMR technique (DOSY, Diffusion Ordered Spectroscopy). With DOSY, a mixture of molecules of very similar size can be readily analysed. As such, this technique is a powerful alternative to physical separation technique for the analysis of complex mixtures such as HPLC.

Erythromycin B was degraded completely and the degradation sample was run in the NMR spectrometer employing the $^1H$-DOSY experiment. A typical DOSY spectrum of degradation sample is presented in FIG. 13. Most of the blobs in the DOSY spectrum are aligned into two rows suggesting there were 2 compounds in the mixture. These blobs could be characterised by the chemical shift of 5-deB. The first row, consisting of the most blobs, is the erythromycin B ring with desosamine sugar still attached to it. Another row of blobs suggest that cladinose sugar has fallen away from the erythromycin B ring. A ROESY (Rotating frame nuclear Overhauser Effect Spectroscopy) experiment was used to support the results.

Figure 14:
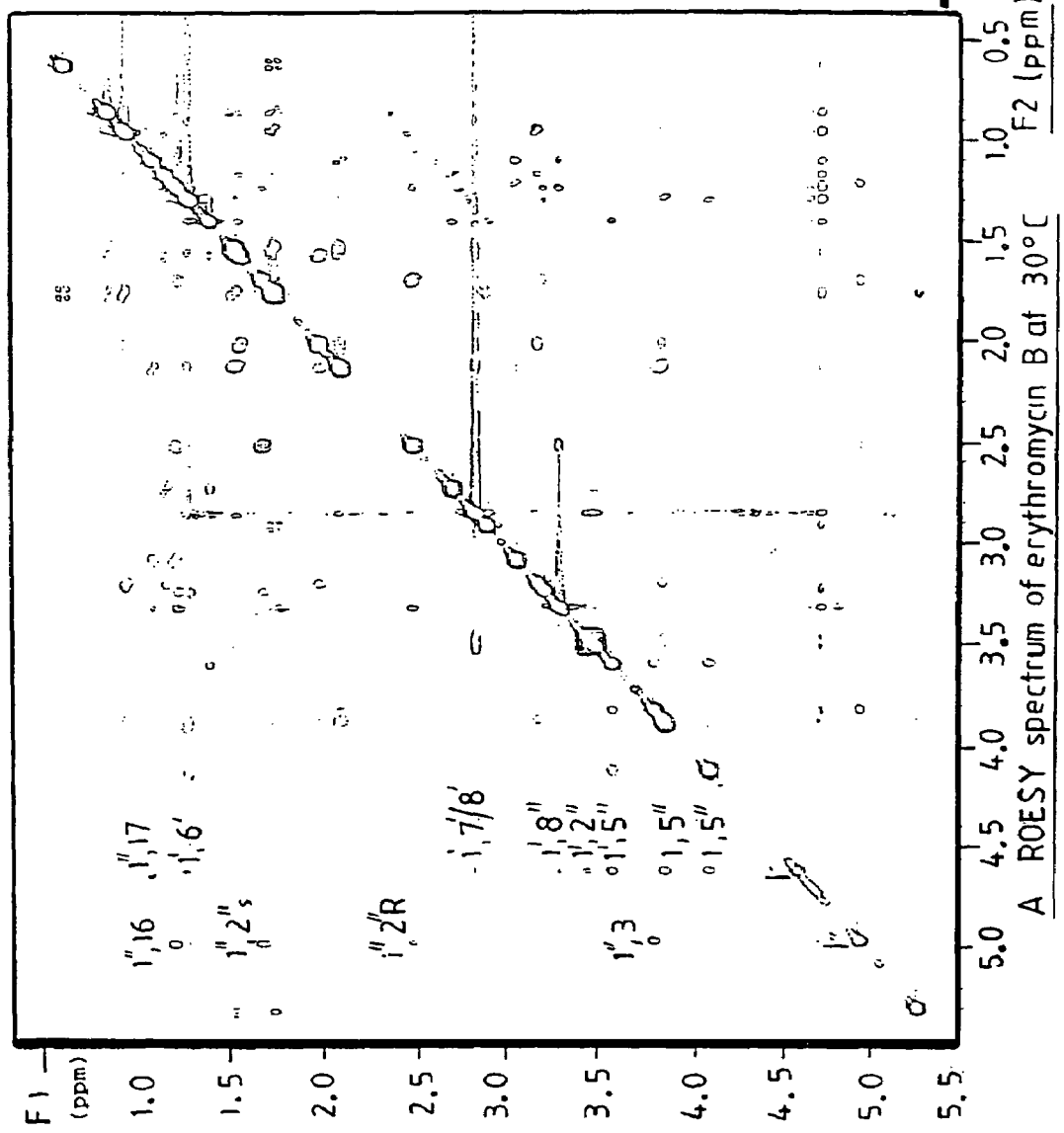
FIG. 14. A ROESY spectrum of Erythromycin B at 30° C.
Figure 15:
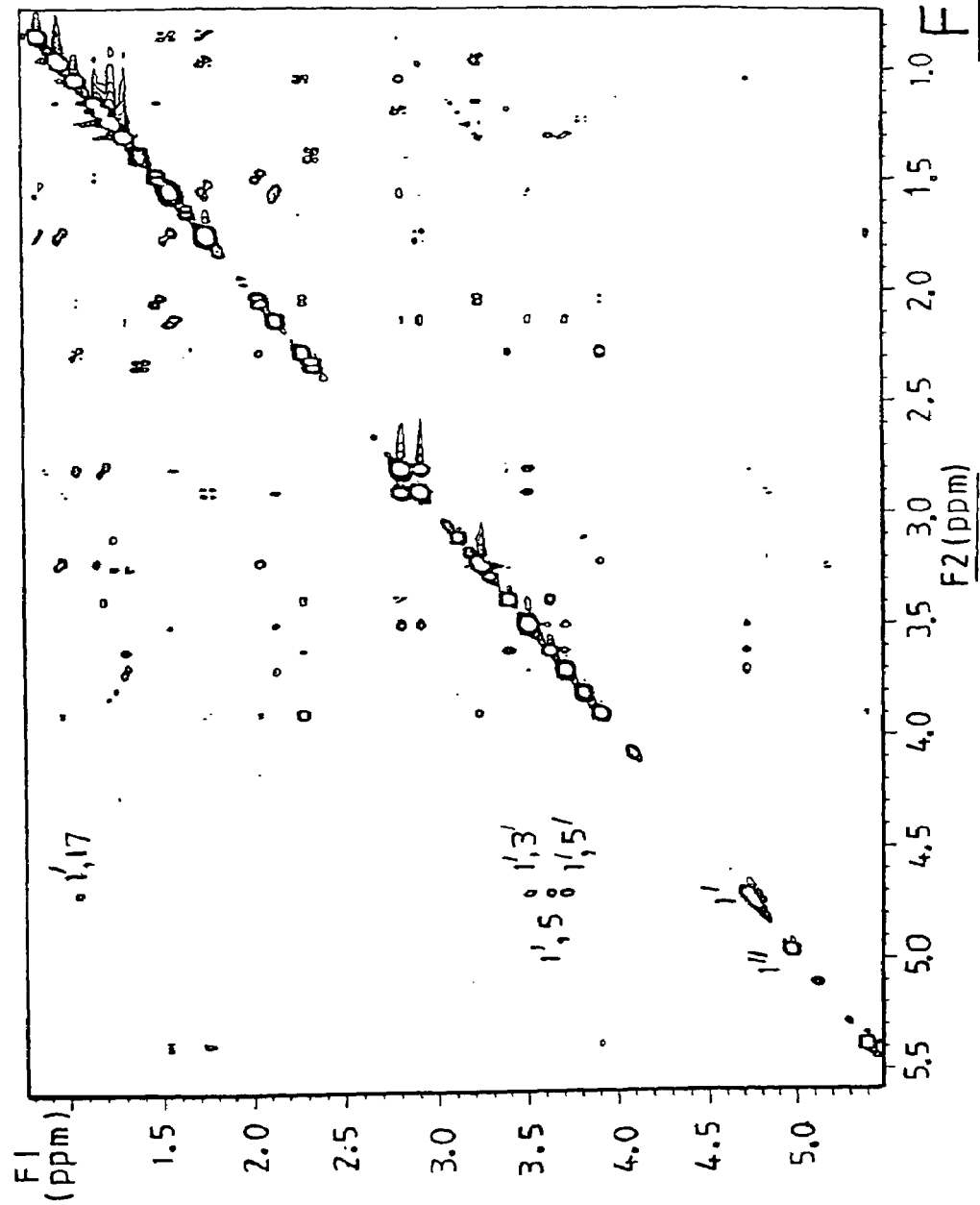
FIG. 15. ROESY spectrum at 30° C. from degradation mixtures of Erythromycin B, containing 5-deB and cladinose.
Figure 16:
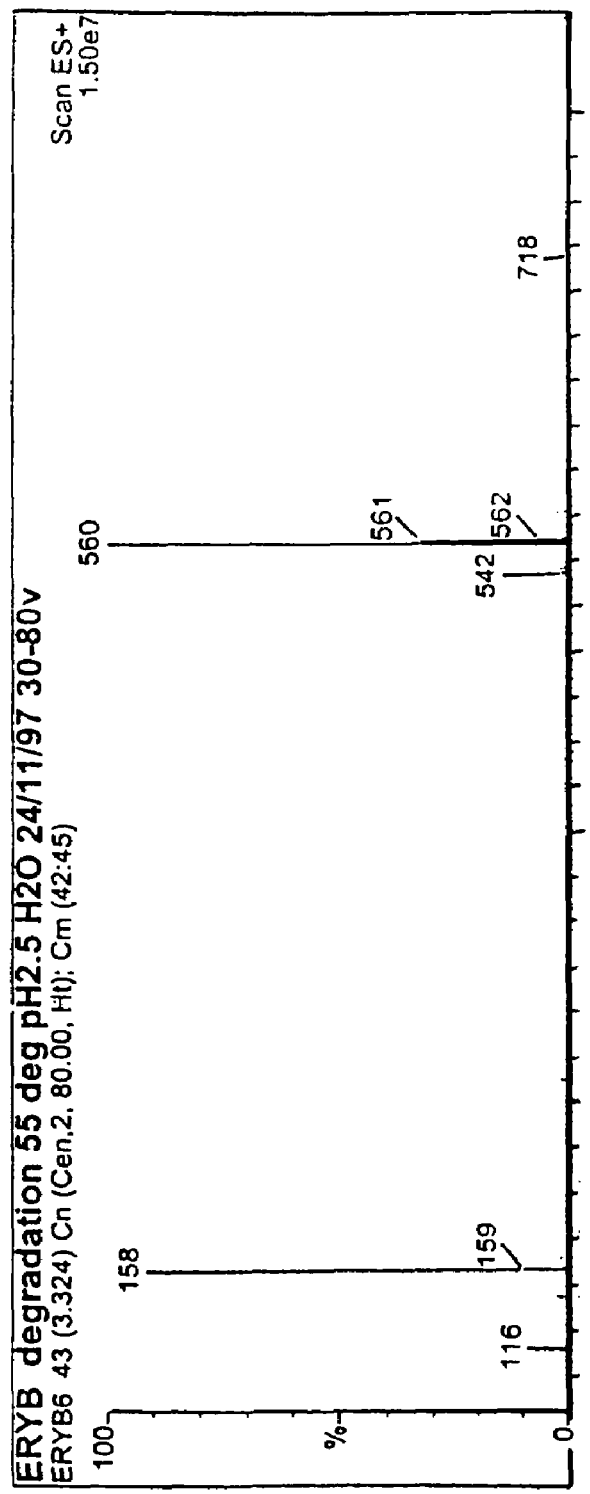
FIG. 16. Electrospray-Mass spectrum (in positive mode) of Erythromycin B (MW 717), 5-deB (MW 559) and cladinose (MW 157) in protiated buffer, pH 2.5. The actual mass of every compound should be less 1 mass unit from the values shown in the spectrum.

The ROESY spectrum of erythromycin B and a degraded sample of erythromycin B, are presented in FIGS. 14 and 15, respectively. In FIG. 14, there are cross-peaks between H1" (in cladinose molecule) to H3 and H16 (in erythromycin B ring), and between H1' (in desosamine molecule) to H5 and H17 (in erythromycin B ring). Cross-peaks occur in this spectrum when two protons are within 5 Angstrom units of each other. In FIG. 15, there are no cross-peaks between H1" to any protons in the erythromycin B ring, however, there are cross-peaks between H1"of desosamine molecule, to protons in the erythonolide B ring. These observations are in agreement to the results of DOSY experiment where cladinose ring has fallen away from the erythromycin B ring, but the desosamine sugar is still intact. Degradation of cladinose has also been reported for erythromycin A analogues such as clarithromycin (Nakagawa et al., 1992) and azithromycin (Fiese & Steffen, 1990) but does not occur to erythromycin A itself(Alan, 1996; Cachet et al., 1989; Atkins et al., 1989). Mass spectrometry was used to obtain the molecular weight of every species in the degradation mixture. A typical mass spectrum of the degradation product of erythromycin B is depicted in FIG. 16. (Note that the actual mass of every compound should be less 1 mass unit from the values shown in the spectrum).

(v) Verification that 5-desosaminyl Erythromycin (5-deB) is the End Product

Figure 17:
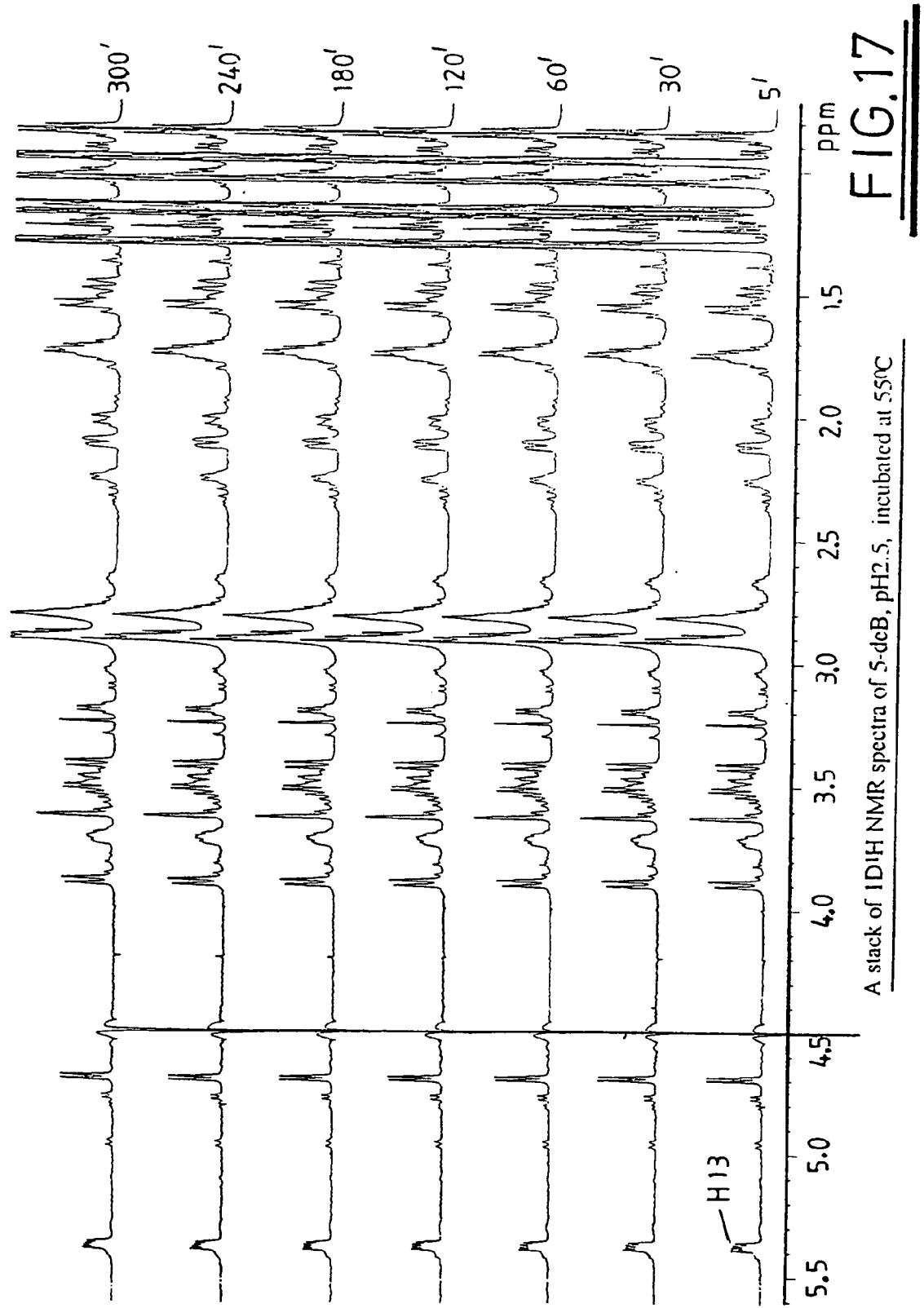
FIG. 17. A stack of $1D^1H$ NMR spectra of 5-deB, pH 2.5, incubated at 55° C.
Figure 18:
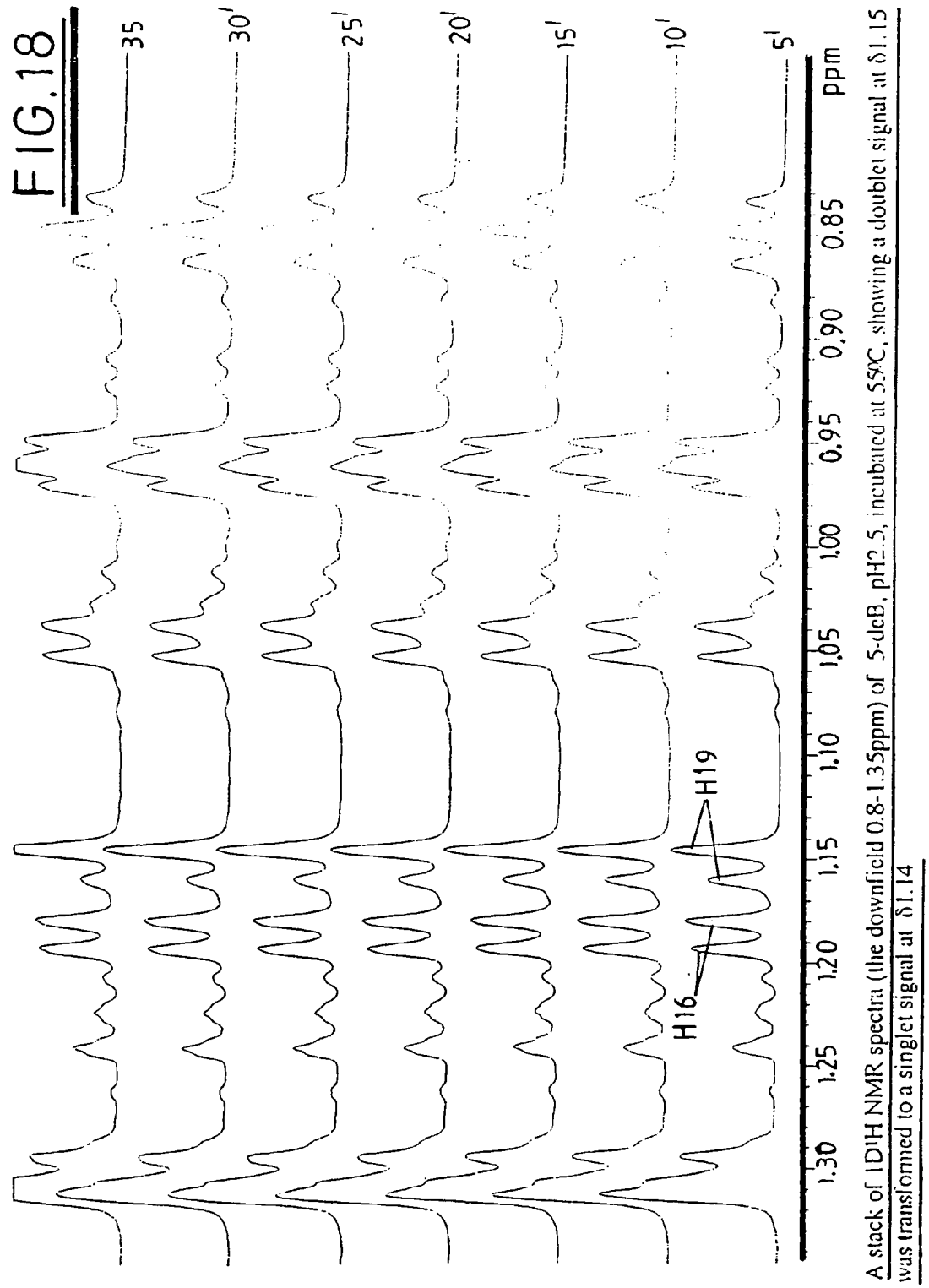
FIG. 18. A stack of $1D^1H$ NMR spectra (the downfield 0.8–1.35 ppm) of 5-deB, pH 2.5, incubated at 55° C., showing a doublet signal at $\delta 1.15$ was transformed to a singlet signal at $\delta 1.14$.

The 5-deB sample in Britton-Robinson buffer, apparent pH 2.5, was degraded at 55° C. for 5 hr and a set of 1D$^1$H spectra was acquired and is depicted in FIG. 17, whilst FIG. 18 shows the downfield 0.80–1.35 ppm region of the spectra. The deuteriation effects at C8 as in erythromycin B were observed but there was no change elsewhere. We postulate that 5-deB does not degrade further under this condition (pH 2.5, 55° C., 5 hr degradation period).

(vi) Identification of Erythromycin B Enolether as the Intermediate in the Degradation Reaction of Erythromycin B In the degradation profile of erythromycin B to 5-deB, it was found that the mass balance was not consistent all the time due to the existence of the other compound(s) (section ii). We believe that erythromycin B enol ether (eBee) takes role as the intermediate in the degradation reaction of erythromycin B, similar to the involvement of erythromycin A enol ether during the decomposition of erythromycin A.

The suspected intermediate, eBee was prepared and then was added into a partially degraded erythromycin B, the mixture of partially degraded erythromycin B, and the pure eBee solution were compared. The singlet signal of H19 at δ1.60 could be used to demonstrate the existence of eBee. However, the experiment was not successful because eBee at pH2.5 was rapidly degraded to erythromycin B and could not be seen in the spectrum. However, the involvement of eBee as the intermediate in the degradation of erythromycin B was clearly observed in the degradation experiment of eBee.

(vii) Degradation of Erythromycin B Enol ether

Figure 2:
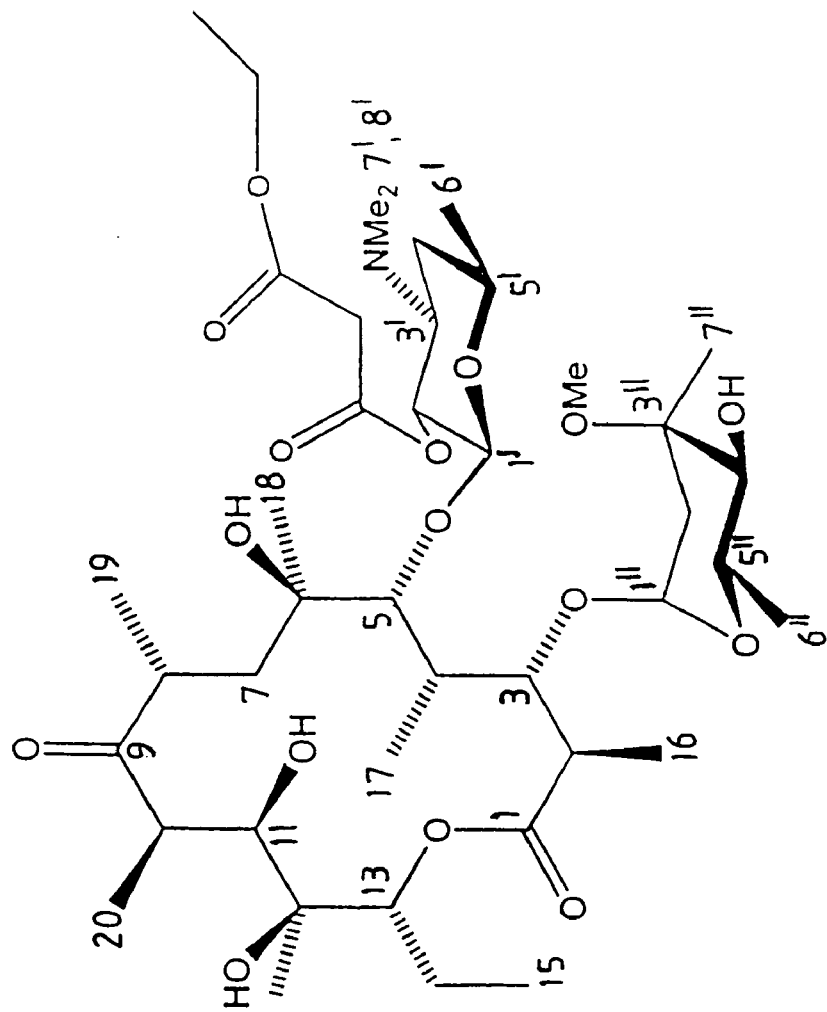
FIG. 2. 5-Erythromycin A ethyl succinate.
Figure 3:
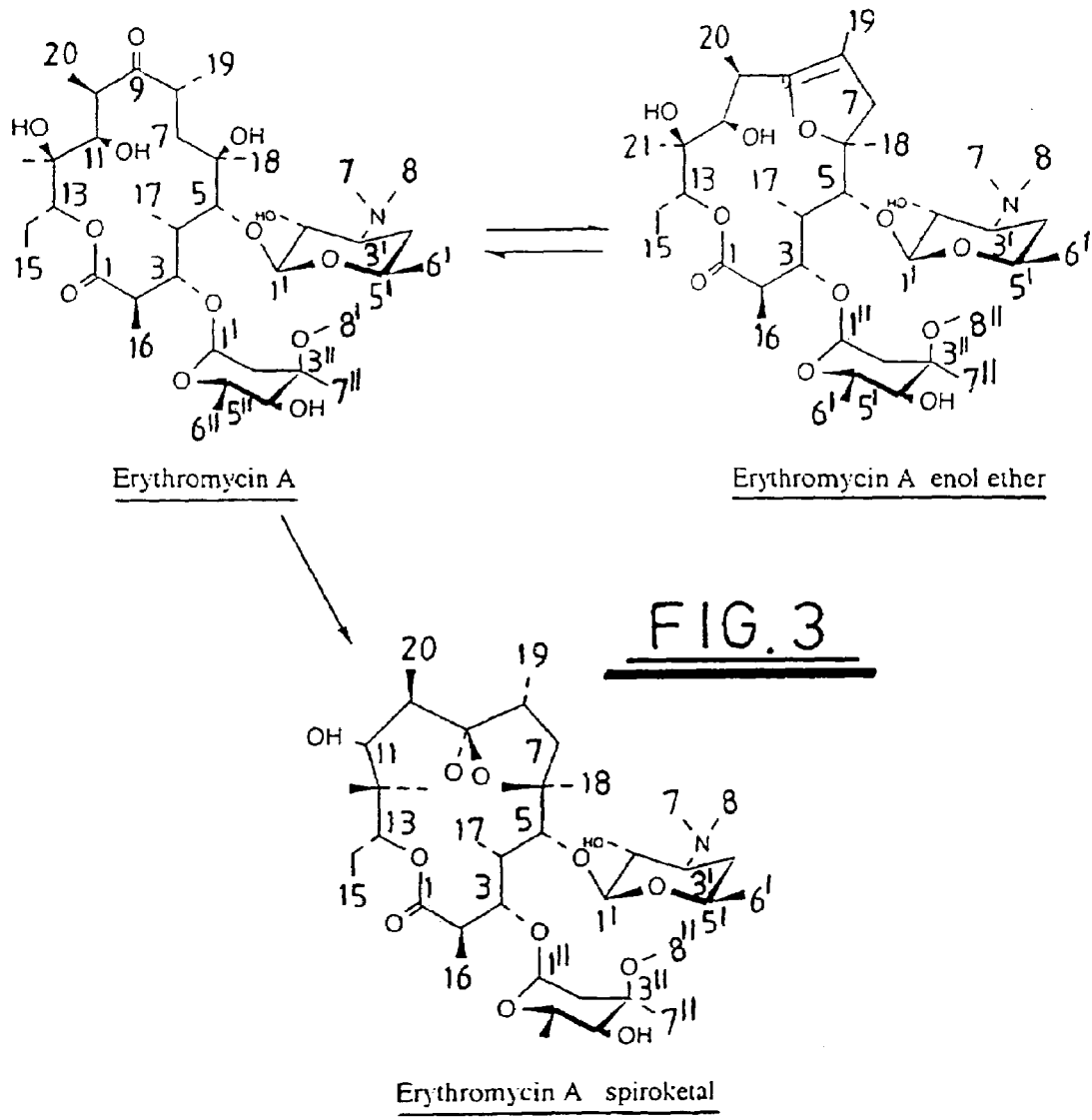
FIG. 3. Decomposition pathway for Erythromycin A in aqueous acidic medium.

Two mechanisms of degradation were proposed for erythromycin A. Atkins and associates (1986) suggested erythromycin A decomposed to anhydroerythromycin A via erythromycin A enol ether (see FIG. 1). Cachet et al. (1989) postulated that during decomposition erythromycin A is in equilibrium with erythromycin A enol ether and simultaneously erythromycin A is directly converted to anhydroerythromycin A (see FIG. 2). The mechanism proposed by Cachet is consistent with the work of Perwaiz (1996) where he concluded that erythromycin A enol ether is degraded to anhydroerythromycin A via erythromycin A.

Figure 19:
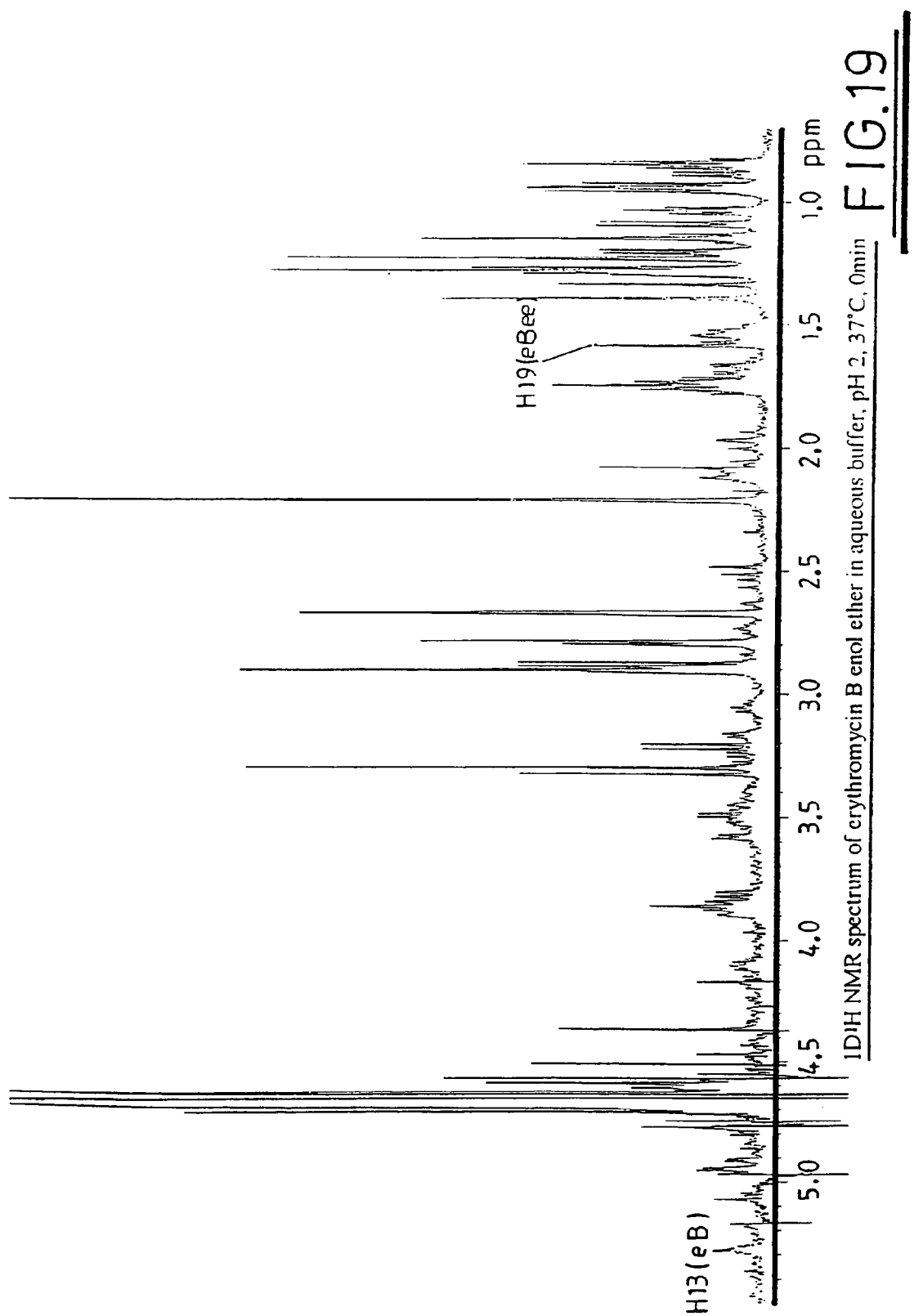
FIG. 19. $1D^1H$ NMR spectrum of Erythromycin B enol ether in aqueous buffer, pH 2, 35° C., 0 min.
Figure 20:
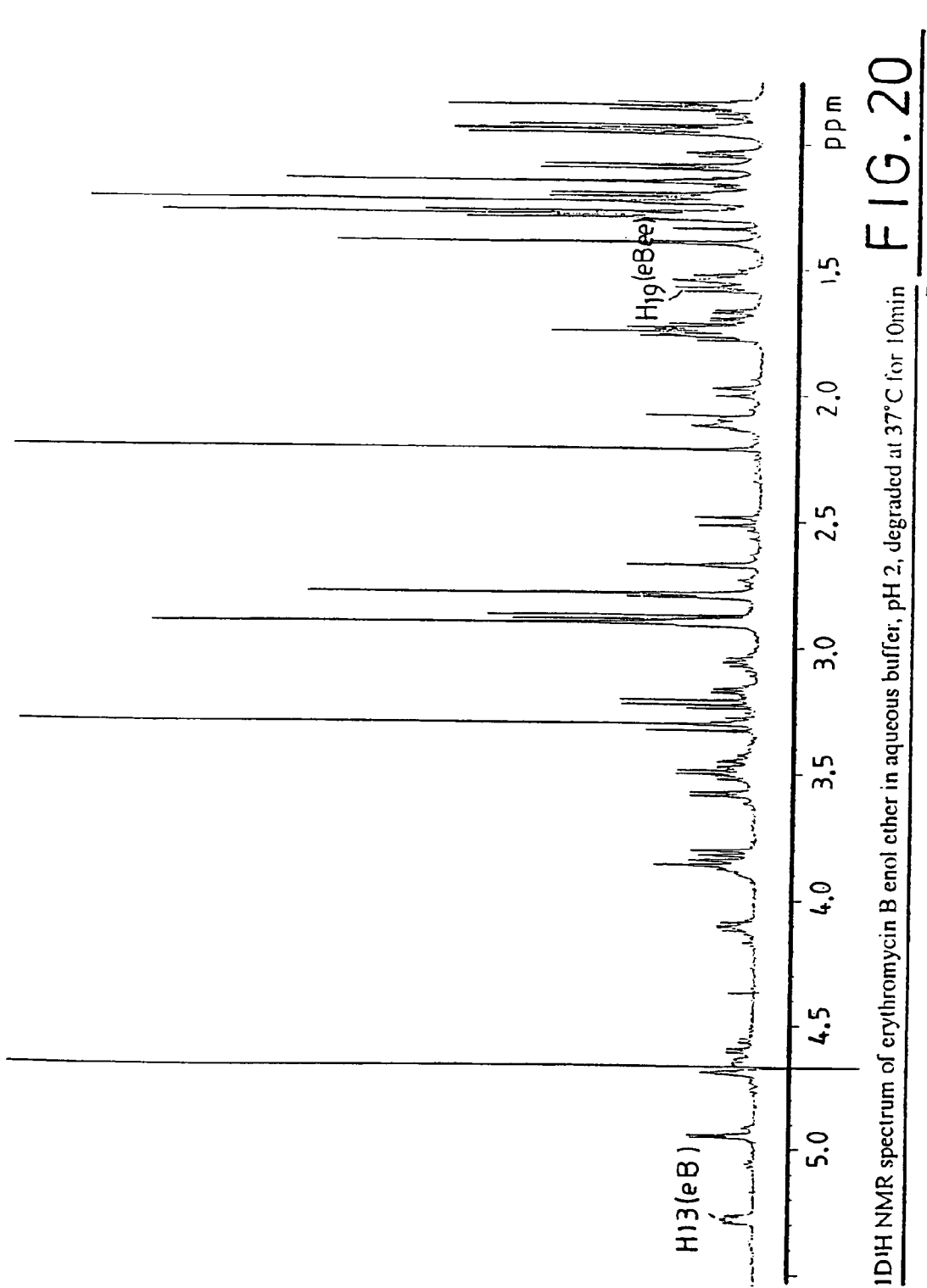
FIG. 20. $1D^1H$ NMR spectrum of Erythromycin B enol ether in aqueous buffer, pH 2, degraded at 37° C., 10 min.
Figure 21:
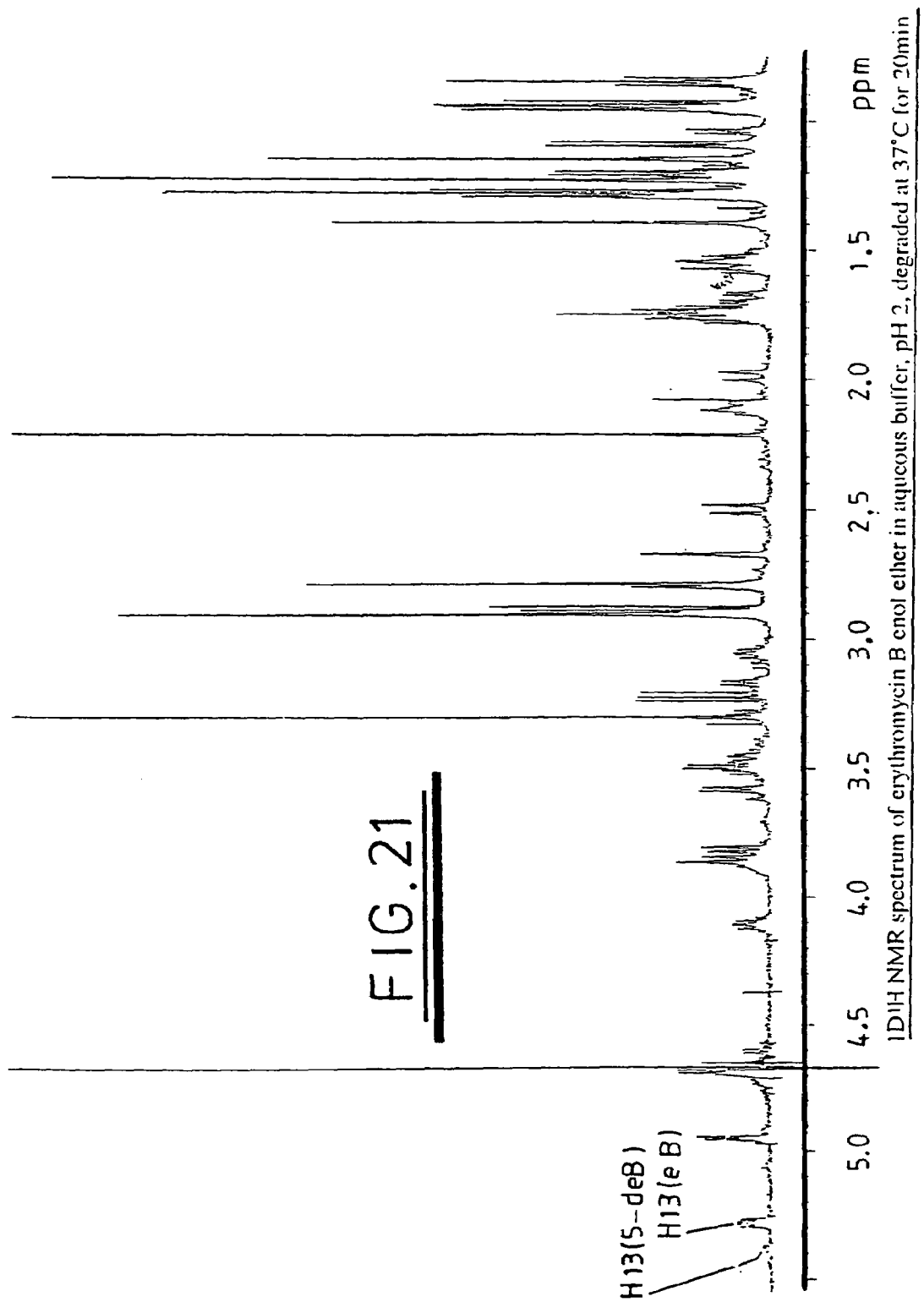
FIG. 21. $1D^1H$ NMR spectrum of Erythromycin B enol ether in aqueous buffer, pH 2, degraded at 37° C., 20 min.

At present, there is no mechanism of degradation of erythromycin B which has been proposed. An experiment was designed to distinguish whether eBee is degraded to 5-deB via erythromycin B or not. Britton-Robinson buffers, 40 mM of pH2 and 7 were prepared and aliquoted into eppendorf tubes. Just before the experiment started, erythromycin B was dissolved in 20 ul of dimethyl-d$_6$ sulfoxide (99.9 atom % D, Sigma, St Louis, USA) and then was transferred immediately into the buffer and 1D$^1$H NMR spectra were recorded at 37° C. The typical spectra at 0, 10 and 20 min are depicted in FIGS. 19, 20 and 21, respectively.

The spectra suggested that at pH2, eBee, characterised by signal H19 at δ1.59, was initially existing together with erythromycin B, identified by its H13 at δ5.29, However, no 5-deB was detected in the spectrum. After 10 min, the amount of eBee was reduced to almost 40%, but 5-deB was still undetectable. After 20 min, 5-deB appeared in the spectrum, characterised by its H13 at δ5.38, whilst eBee became insignificant in the spectrum. Spectra at 30 min and onwards demonstrating a typical degradation of erythromycin B where the amount of erythromycin B decreased whilst the amount of 5-deB increased over time.

Figure 22:
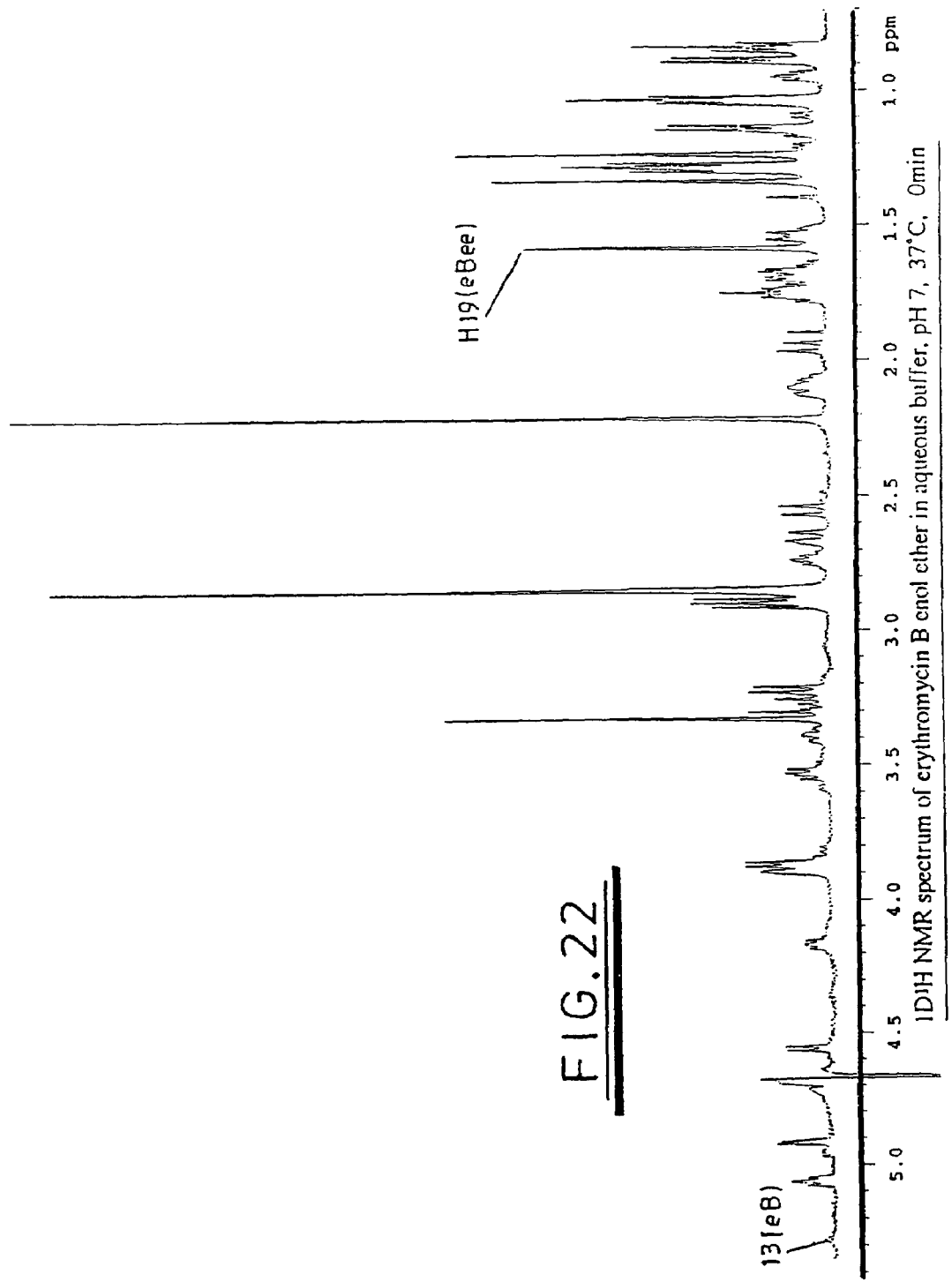
FIG. 22. $1D^1H$ NMR spectrum of Erythromycin B enol ether in aqueous buffer, pH 7, 37° C., 0 min.
Figure 23:
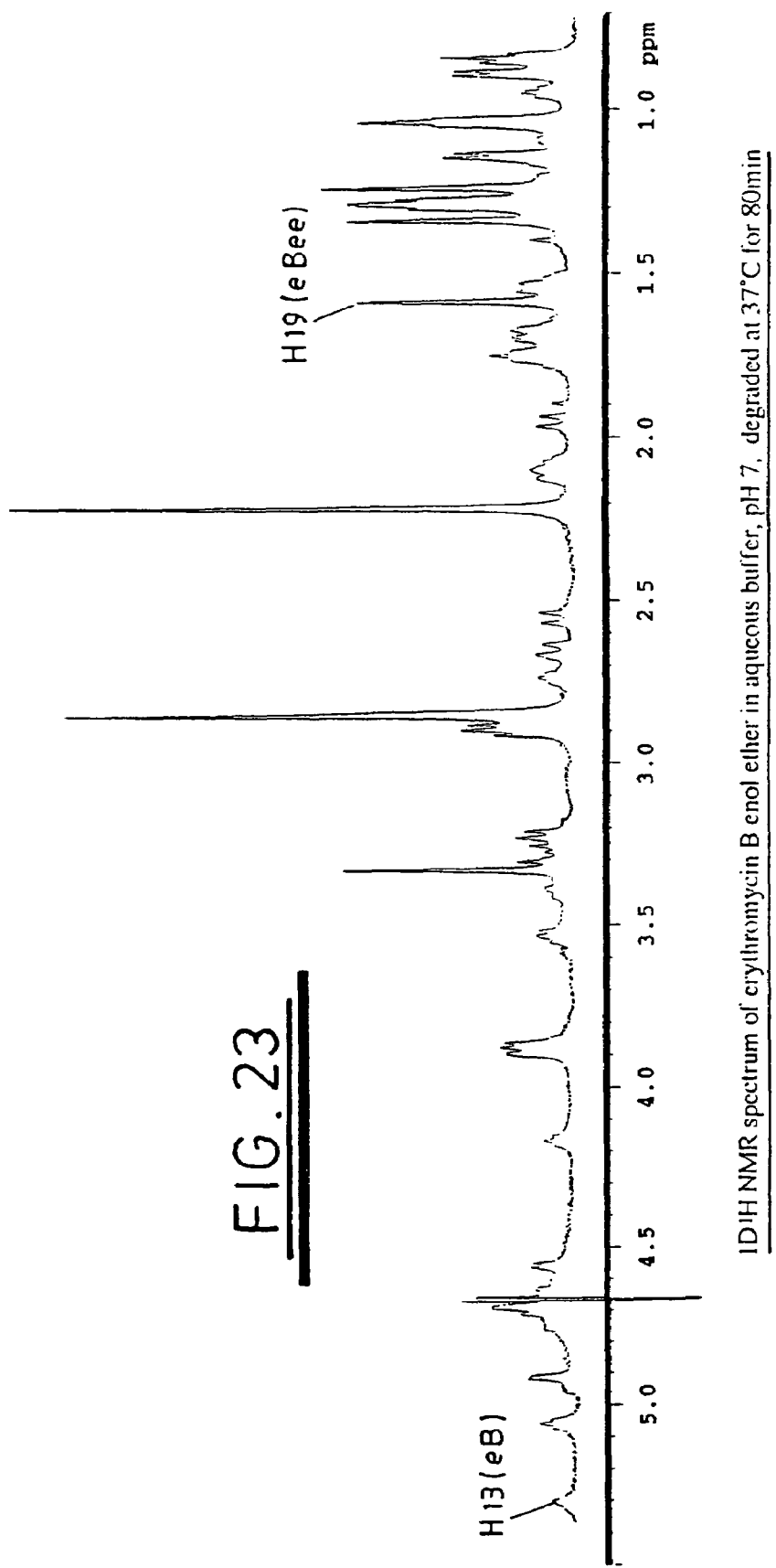
FIG. 23. $1D^1H$ NMR spectrum of Erythromycin B enol ether in aqueous buffer, pH 7, degraded at 37° C., 80 min.

A similar experiment was repeated by using buffer at pH 7, and 1D$^1$H spectra were recorded at 37° C. The spectrum of eBee after 0 and 60 min of incubation are depicted in FIGS. 22 and 23, respectively. The spectra at pH7 showed that eBee was not degraded at least for 80 min where the experiment had been carried out. There was trace of erythromycin B but no eBee was detected in the spectra.

Both results at pH2 and 7 suggested that eBee in a solution can be converted to erythromycin B, and subsequently, erythromycin B can be converted to 5-deB. This reaction is very much dependent on the acidity of the environment. However, the actual mechanism of reaction is still not clear.

For example, by comparing the degradation rate of eBee and erythromycin B to 5-deB, we could possibly say that eBee degrades via erythromycin B, if eBee degrades at least at the same rate as erythromycin B or maybe slower. The degradation mechanism below could be suggested:

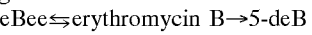
eBee⇌erythromycin B→5-deB

However, if eBee degrades at least the same rate as erythromycin B or faster, we could suggest that erythromycin B degrades via eBee as shown below:

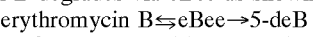
erythromycin B⇌eBee→5-deB

So far, we are unable to postulate the reaction mechanism of erythromycin B. However, the results suggest that eBee could possibly be a prodrug of erythromycin B. In acid environment of the stomach, eBee will be converted to erythromycin B and depending on the gastric emptying time, erythromycin B could possibly survive decomposition and enter the intestine as an intact form where it could be absorbed into the blood circulation.

REFERENCES

[1] IO Kibwaga, J. Hoogmartens, E. Roets, H. Vanderharghe, L. Verbist, M. Dubost, C. Pascal, P. Petitjean and G. Levol, Antimicrob. Agents Chemother. 1985, 28, 630.
[2] P. S. Alam, Ph.D. Thesis, University of Manchester, 1997.
[3] P J Atkins, T O Herbert and N B Jones, Int. J. Pharm. 1986, 30, 199.
[4] T. Cachet, G V Mooter, R. Hauchecorne, C. Vinckier and J. Hoogmartens, Int. J. Pharm. 1989, 55, 59.
[5] E F Fiese and S H Steffen, J. Antimicrob. Chemother. 1990, 25 (suppl. A), 39.
[6] Y. Nakagawa, S. Itai, T. Yoshida and T. Nagai, Chem. Pharm. Bull. (Japan) 1992, 40, 725.

Alam, P. S., in "*The study of drug degradation using nuclear magnetic resonance spectroscopy*", PhD Thesis, dept. Pharmacy, Univ. Manchester, 1996.

Alam, P. S., Buxton, P. C., Parkinson, J. A. and Barber, J., *J. Chem. Soc. Perkin. Trans.* 2., 1163, 1995.

Amer, M. M. and Takla, K. F., *Bull. Faculty Pharmacy Cairo University*, 15, 325, 78.

Atkins, P. J., Herbert, T. O. and Jones, N. B., *Int. J. Pharmaceutics*, 30, 199, 1986.

Atkins, P. W., et al., in *"Principles of Physical Chemistry"*, Pitman, London, 1983.

Barber, J., Gyi, J. I., Lian, L., Morris, G. A., Pye, D. A. and Sutherland, J. K., *J. Chem. Soc. Perkin. Trans.* 2., 1489, 1991.

Barber, J., Gyi, J. I., Lian, L., Morris, G. A., Pye, D. A. and Sutherland, J. K., *J. Chem. Soc. Chem. Comm.*, 1040, 1990.

Barroso, M. B., Alonso, R. M. and Jimenez, R. M., *Anal. Chim. Acta.*, 305, 332, 1995.

Bell, R. P., in *"Acid-base Catalysis"*, Oxford University Press, London, 1941.

Brittain, D. P., *Med. Clin. N. Am.*, 71, 1147, 1987.

Cachet, T. H., Van den Mooter, G., Hauchecorne, R., Vinckier, C. and Hoogmartens, J., *Int. J. Pharm.*, 55, 59, 1989.

Carestensen, J. T., in *"Drug stability: Prnciples and Practises"*, Marcel Dekker, New York, 11, 1990.

Contreras, J. T. and Vasquez, D., *Eur. J. Biochem.*, 74, 539, 1977.

Fiese, E. F. and Steffen, S. H., *J. Antimicrob. Chemother.*, 25 (Suppl A), 39, 1990.

Ghebre-Sellassie, I., Hem, S. L. and Knevel, A. M., *J. Pharm. Sci.*, 73, 125, 1984.

Hinselwood, C. N., *"The Kinetics of Chemical Change"*, Oxford University Press, London, 1940.

Hollis, D. P., *Anal. Chem.*, 35, 1682, 1963.

Inatomi, N., Satoh, H., Satoh, T., Itoh, Z. and Omura, S., *Eur. J. Pharmacol.*, 183, 2183, 1990.

Janssens, J., Peeters, T. L., Vantrappen, G., Tack, J., Urbain, J. L., De Roo, M., Muls, E. and Bouillon, R., *N. Engl. J. Med.*, 322, 1028, 1990.

Kim, S. K., Jung, M. Y. and Kim, S. Y., *Food. Chem.*, 59, 273, 1997.

Kirst, H. A., in *"Progress in Medicinal Chemistry"*, Ellis, G. P. and Luscombe, D. K. (Eds), Elsevier Science Publisher, Vol 30, 57, 1993.

Kirst, H. A., in *"Kirk-Othmer Encyclopedia of Chemical Technology"*, 4th Ed, Wiley, New York, Vol 3, 169, 1992.

Kitamura, S., Tada, T., Okamoto, Y. and Yasuda, T., *Pharm. Res.*, 9, 138, 1992.

Kondrat'eva, A. P. and Burns, B. P., *Antibiotik*, 7, 571, 1962.

Krowicki, K. and Zamosjski, A., *J. Antibiotics.*, 26, 58, 1973.

Kucers, A. and Bennet, N. M. in *"The use of Antibiotics, A comprehensive review with clinical emphasis"*, 4th Ed, Heineman, Oxford, 851, 1989.

Kurath, P. and Egan, R. S., *Hiv. Chim. Acta.*, 54, 523, 1971.

Labeda, D. P., *Int. J. Syst. Bacteriol.*, 37, 19, 1987.

Laidler, K. J., in *"Chemical Kinetics"*, 2nd Ed., McGraw-Hill Book Co Inc., N.Y., 1965.

Lerner, D. A., Bonneford, G., Fabre, H., Mondru, B. and deBuochberg, M. S., *J. Pharm. Sci.*, 77, 699, 1988.

McGuire, J. M., Bunch, R. L., Anderson, R. C., Boaz, H. E., Flynn, E. H., Powell, H. M. and Smith, J. W., *Antibiot. Chemother.*, 2, 281, 1952.

Menninger, J. R. and Otto, D. P., *Antimicrob. Agents Chemother.*, 21, 811, 1982.

Mitsumori, F., Arata, Y., Fujiwara, S. and Muranka, M., *Bull. Chem. Soc. Japan.*, 50, 3164, 1977.

Moore, J. W. and Pearson, R. G., in *"Kinetics and Mechanism"*, John Willy & Sons, N.Y., 1981.

Nakagawa, Y., Itai, S., Yoshida, T. and Nagai, T., *Chem. Pharm. Bull.*, 40, 725, 1992.

Omura, S., Tsuzuki, K., Sunazuka, T., Marui, S., Toyoda, H., Inatomi, N. and Itoh, Z., *J. Med. Chem.*, 30, 1941, 1987.

Pye, D. A., Gyi, J. I., and Barber, J., *J. Chem. Soc. Chem. Comm.*, 1143, 1990.

Raez, I. in *"Drug Formulation"*, John Willy & Sons, N.Y., 1989.

Ruckmick, S. C. and Duong, S. T., *J. Pharm. Sci.*, 84, 502, 1995.

Stephen, V. C. and Conine, J. W in *"Antibiotics Annual 1958–59"*, Welch, H. and Marti-Ibanez, F. (Eds), Medical Encyclopedia Inc., 346, 1959.

Sunazuka, T., Tsuzuki, K., Marui, S., Toyoda, H., Omura, S., Inatomi, N. and Itoh, Z., *Chem. Pharm. Bull.*, 37, 2701, 1989.

Tait-Kamradt, A., Clancey, J., Cronan, M., Dib-Hajj, F., Wondrack, L., Yuan, W. and Sutcliffe, J., *Antimicrob. Agents Chemother.*, 41, 2251, 1997.

Teraoka, H. and Nierhaus, K. H., *J. Mol. Biol.*, 126, 185, 1978.

Tsuzuki, K., Sunazuka, T., Marui, S., Toyoda, H., Omura, S., Inatomi, N. and Itoh, Z., *Chem. Pharm. Bull.*, 37, 2687, 1989.

Vinckier, C., Hauchecorne, R., Cachet, T., Van de Mooter, G. and Hoogmartens, J., *Int. J. Pharm.*, 55, 67, 1989.

Visconti, M., Citerio, L., Borsa, M. and Pifferi, G., *J. Pharm. Sci.*, 73, 1812, 1984.

Wang, D. and Notari, E., *J. Pharm. Sci.*, 83, 577, 1974.

What is claimed is:

1. A method of treating a bacterial infection comprising administering to a patient in need of such treatment a therapeutically effective amount of an antibiotic agent, wherein said antibiotic agent is a 2' ester of Erythromycin B with a dicarboxylic acid or a 2'-carboxylic acid ester of Erythromycin B enol ether.

2. The method as claimed in claim 1 wherein the antibiotic agent is a 2'-ester of Erythromycin B enol ether with a monocarboxylic acid.

3. The method as claimed in claim 1 wherein the antibiotic agent is 2'-ester of Erythromycin B enol ether with a dicarboxylic acid.

4. The method as claimed in claim 3 wherein the ester is a succinate ester.

5. The method as claimed in claim 1 wherein the 2' carboxylic acid ester of Erythromycin B is a succinate ester.

6. The method as claimed in claim 1 wherein the antibiotic agent is administered in an amount of up to 500 mg per day.

7. The method as claimed in claim 1 wherein the antibiotic agent is administered in an amount of 250 to 500 mg per day.

8. The method as claimed in claim 1 wherein the antibiotic agent is administered in the form of a tablet, a capsule, an elixir, an injectable or a syrup.

9. The method as claimed in claim 1 wherein the bacterial infection is TB, Syphilis, *Helicobacter pylori* or Chlamydia.

10. An antibiotic composition comprising a therapeutically effective amount of an antibiotic agent, wherein said antibiotic agent is a 2' ester of Erythromycin B with a dicarboxylic acid or a 2'-carboxylic acid esters of Erythromycin B enol ether.

11. The composition as claimed in claim 10 wherein the antibiotic agent is a 2'-ester of Erythromycin B enol ether with a monocarboxylic acid.

12. The composition as claimed in claim 10 wherein the antibiotic agent is 2'-ester of Erythromycin B enol ether with a dicarboxylic acid.

13. The composition as claimed in claim 12 wherein the ester is a succinate ester.

14. The composition as claimed in claim 10 wherein the 2' carboxylic acid ester of Erythromycin B is a succinate ester.

15. A 2'-carboxylic acid ester of Erythromycin B enol ether.

16. The ester as claimed in claim 15 which is a 2'-ester of Erythromycin B enol ether with a monocarboxylic acid.

17. The ester as claimed in claim 15 which is a 2'-ester of Erythromycin B enol ether with a dicarboxylic acid.

18. The ester as claimed in claim 17 wherein the ester is a succinate ester.

19. A 2'-ester of Erythromycin B with a dicarboxylic acid.

20. The ester as claimed in claim 19 which is a succinate ester.

* * * * *